US012303369B2

(12) United States Patent
Ducker et al.

(10) Patent No.: US 12,303,369 B2
(45) Date of Patent: May 20, 2025

(54) ABSORBENT LAMINATES, ABSORBENT CORES AND DISPOSABLE ARTICLES UTILIZING THE ABSORBENT LAMINATES, AND RELATED METHODS

(71) Applicant: ATTENDS HEALTHCARE PRODUCTS, INC., Greenville, NC (US)

(72) Inventors: Paul M. Ducker, Saint Simons Island, GA (US); Harry J. Chmielewski, Wake Forest, NC (US)

(73) Assignee: ATTENDS HEALTHCARE PRODUCTS, INC.

( * ) Notice: Subject to any disclaimer, the term of this patent is extended or adjusted under 35 U.S.C. 154(b) by 1028 days.

(21) Appl. No.: 16/466,245

(22) PCT Filed: Dec. 14, 2017

(86) PCT No.: PCT/US2017/066467
§ 371 (c)(1),
(2) Date: Jun. 3, 2019

(87) PCT Pub. No.: WO2018/112229
PCT Pub. Date: Jun. 21, 2018

(65) Prior Publication Data
US 2020/0060895 A1    Feb. 27, 2020

Related U.S. Application Data

(60) Provisional application No. 62/505,218, filed on May 12, 2017, provisional application No. 62/434,156, filed on Dec. 14, 2016.

(51) Int. Cl.
*A61F 13/15*      (2006.01)
*A61F 13/534*     (2006.01)
(Continued)

(52) U.S. Cl.
CPC .......... *A61F 13/534* (2013.01); *A61F 13/513* (2013.01); *A61F 2013/530547* (2013.01);
(Continued)

(58) Field of Classification Search
CPC .. A61F 13/534; A61F 13/513; A61F 2013/53; B32B 5/022; B32B 5/08;
(Continued)

(56) References Cited

U.S. PATENT DOCUMENTS

| 3,563,243 A | 2/1971 | Lindquist |
| 3,699,966 A | 10/1972 | Chapuis |

(Continued)

FOREIGN PATENT DOCUMENTS

| CN | 1230396 | 10/1999 |
| CN | 1303255 | 7/2001 |

(Continued)

OTHER PUBLICATIONS

Office Action Issued in Corresponding Chinese Patent Application No. 201780085920.X, dated Jan. 22, 2021.
(Continued)

*Primary Examiner* — Jacqueline F Stephens
(74) *Attorney, Agent, or Firm* — Norton Rose Fulbright US LLP

(57) ABSTRACT

Absorbent multi-layer laminates with SAP on both sides of a middle substrate that comprises wettable cellulosic fibers. Also absorbent cores including such absorbent laminates. Absorbent articles such as protective underwear, adult briefs, baby diapers and nursing pads including such absorbent cores, and patient-support pads such as underpads and sacral pads including such absorbent laminates and cores.

20 Claims, 11 Drawing Sheets

(51) Int. Cl.
  *A61F 13/513* (2006.01)
  *A61F 13/53* (2006.01)
  *B32B 5/02* (2006.01)
  *B32B 5/08* (2006.01)
  *B32B 7/12* (2006.01)

(52) U.S. Cl.
  CPC ............ *A61F 2013/530613* (2013.01); *A61F 2013/5307* (2013.01); *B32B 5/022* (2013.01); *B32B 5/08* (2013.01); *B32B 7/12* (2013.01); *B32B 2262/062* (2013.01); *B32B 2307/54* (2013.01); *B32B 2307/726* (2013.01); *B32B 2309/105* (2013.01)

(58) Field of Classification Search
  CPC ... B32B 7/12; B32B 2262/06; B32B 2307/54; B32B 2307/72; B32B 2309/10
  See application file for complete search history.

(56) References Cited

U.S. PATENT DOCUMENTS

| | | |
|---|---|---|
| 3,863,637 A | 2/1975 | MacDonald et al. |
| 3,865,112 A | 2/1975 | Roeder |
| 4,100,324 A | 7/1978 | Anderson |
| 4,114,621 A | 9/1978 | Mims, Jr. |
| 4,443,512 A | 4/1984 | Delvaux |
| 4,548,116 A | 10/1985 | Yoshida et al. |
| 4,573,986 A | 3/1986 | Minetola et al. |
| 4,576,596 A | 3/1986 | Jackson |
| 4,670,011 A | 6/1987 | Mesek |
| 4,743,246 A | 5/1988 | Lawson |
| 4,752,351 A | 6/1988 | Lunt |
| 4,794,028 A | 12/1988 | Fischer |
| 4,808,177 A | 2/1989 | Desmarais et al. |
| 4,857,067 A | 8/1989 | Wood et al. |
| 4,895,569 A | 1/1990 | Wilson et al. |
| 4,940,464 A | 7/1990 | Van Gompel et al. |
| 4,999,067 A | 3/1991 | Erb et al. |
| 5,021,051 A | 6/1991 | Takashi |
| 5,458,592 A | 10/1995 | Abuto et al. |
| 5,462,538 A | 10/1995 | Korpman |
| 5,486,167 A | 1/1996 | Dragoo et al. |
| 5,494,622 A | 2/1996 | Heath et al. |
| 5,520,673 A | 5/1996 | Yarbrough et al. |
| 5,552,012 A | 9/1996 | Morris et al. |
| 5,558,655 A | 9/1996 | Jezzi et al. |
| 5,562,645 A | 10/1996 | Tanzer et al. |
| 5,593,399 A | 1/1997 | Tanzer et al. |
| 5,624,426 A | 4/1997 | Roe et al. |
| 5,643,243 A | 7/1997 | Klemp |
| 5,646,180 A | 7/1997 | Chaturvedi |
| 5,649,916 A | 7/1997 | DiPalma |
| 5,713,111 A | 2/1998 | Hattori et al. |
| 5,735,838 A | 4/1998 | Roennberg et al. |
| 5,735,984 A | 4/1998 | Hoff et al. |
| 5,785,696 A | 7/1998 | Inoue et al. |
| 5,795,640 A | 8/1998 | Billarant |
| 5,800,672 A | 9/1998 | Boyce et al. |
| 5,803,920 A | 9/1998 | Gilman |
| 5,879,494 A | 3/1999 | Hoff et al. |
| 5,904,675 A | 5/1999 | Robinson et al. |
| 5,919,493 A | 7/1999 | Sheppard et al. |
| 5,944,706 A | 8/1999 | Palumbo et al. |
| 5,968,027 A | 10/1999 | Cole |
| 5,989,008 A | 11/1999 | Wytkin |
| 6,037,518 A | 3/2000 | Guidotti et al. |
| 6,054,091 A | 4/2000 | Miller et al. |
| 6,149,638 A | 11/2000 | Vogt |
| 6,159,190 A | 12/2000 | Mitsugu et al. |
| 6,165,298 A | 12/2000 | Samida et al. |
| 6,174,302 B1 | 1/2001 | Yoshinori |
| 6,191,340 B1 | 2/2001 | Carlucci et al. |
| 6,248,276 B1 | 6/2001 | Parellada et al. |
| 6,316,687 B1 | 11/2001 | Davis et al. |
| 6,326,525 B1 | 12/2001 | Hamajima |
| 6,372,953 B1 | 4/2002 | Young et al. |
| 6,380,456 B1 | 4/2002 | Goldman |
| 6,436,234 B1 | 8/2002 | Chen et al. |
| 6,455,114 B1 | 9/2002 | Goldhirsch et al. |
| 6,478,784 B1 | 11/2002 | Johnson et al. |
| 6,479,415 B1 | 11/2002 | Erspamer et al. |
| 6,481,063 B2 | 11/2002 | Shepard et al. |
| 6,540,497 B1 | 4/2003 | Fuda et al. |
| 6,544,245 B2 | 4/2003 | Neeb et al. |
| 6,610,903 B1 | 8/2003 | Latimer et al. |
| 6,632,209 B1 | 10/2003 | Chmielewski |
| 6,645,330 B2 | 11/2003 | Pargass et al. |
| 6,646,180 B1 | 11/2003 | Chmielewski |
| 6,667,424 B1 | 12/2003 | Hamilton et al. |
| 6,675,702 B1 | 1/2004 | Maksimow |
| 6,746,434 B2 | 6/2004 | Johnson et al. |
| 6,746,976 B1 | 6/2004 | Urankar et al. |
| 6,764,478 B2 | 7/2004 | Langdon et al. |
| 6,794,557 B1 | 9/2004 | Klemp |
| 6,827,893 B2 | 12/2004 | Clune |
| 6,851,161 B2 | 2/2005 | Kingsford et al. |
| 6,923,926 B2 | 8/2005 | Walter et al. |
| 6,976,978 B2 | 12/2005 | Ruman et al. |
| 6,991,843 B2 | 1/2006 | Armela et al. |
| 7,032,278 B2 | 4/2006 | Kurtz, Jr. |
| 7,048,818 B2 | 5/2006 | Krantz et al. |
| 7,052,636 B2 | 5/2006 | Ausen et al. |
| 7,052,638 B2 | 5/2006 | Clarner et al. |
| 7,056,462 B2 | 6/2006 | Provost et al. |
| 7,172,008 B2 | 2/2007 | Vanbenschoten et al. |
| 7,175,613 B2 | 2/2007 | Sugiyama et al. |
| 7,223,314 B2 | 5/2007 | Provost |
| 7,232,300 B2 | 6/2007 | Walter |
| 7,275,290 B2 | 10/2007 | Clarner et al. |
| 7,451,532 B2 | 11/2008 | Provost et al. |
| 7,479,195 B2 | 1/2009 | Leidig et al. |
| 7,527,618 B2 | 5/2009 | Benning et al. |
| 7,640,637 B2 | 1/2010 | Efremova et al. |
| 7,727,440 B2 | 6/2010 | Armela et al. |
| 7,910,797 B2 | 3/2011 | Nandrea et al. |
| RE42,475 E | 6/2011 | Armela et al. |
| 7,971,526 B2 | 7/2011 | Blenke et al. |
| 8,021,998 B2 | 9/2011 | Qin et al. |
| 8,039,684 B2 | 10/2011 | Guidotti et al. |
| 8,236,231 B2 | 8/2012 | Ferguson et al. |
| 8,449,807 B2 | 5/2013 | Ferguson et al. |
| 8,549,714 B1 | 10/2013 | Shepard et al. |
| 8,562,580 B2 | 10/2013 | Van Gompel et al. |
| 8,637,136 B2 | 1/2014 | Ferguson et al. |
| 8,778,243 B2 | 7/2014 | Shepard et al. |
| 8,784,722 B2 | 7/2014 | Rocha |
| 9,238,089 B2 | 1/2016 | Chmielewski et al. |
| 9,289,033 B2 | 3/2016 | Cheng |
| 9,398,986 B2 | 7/2016 | Pasqualoni et al. |
| 9,662,248 B2 | 5/2017 | Van Gompel et al. |
| 9,789,012 B2 | 10/2017 | Chmielewski |
| 10,092,674 B2 | 10/2018 | Chmielewski et al. |
| 10,166,156 B2 | 1/2019 | Yeoh |
| 11,007,095 B2 | 5/2021 | Sillerstrom |
| 2001/0031956 A1 | 10/2001 | Drevik |
| 2002/0072725 A1 | 6/2002 | Kolby-Falk |
| 2002/0115969 A1 | 8/2002 | Maeda et al. |
| 2002/0128625 A1 | 9/2002 | Masahito et al. |
| 2003/0018311 A1 | 1/2003 | Graef et al. |
| 2003/0023225 A1 | 1/2003 | Sayama et al. |
| 2003/0041953 A1 | 3/2003 | Farell et al. |
| 2003/0085492 A1 | 5/2003 | Schulte |
| 2003/0105442 A1 | 6/2003 | Johnston et al. |
| 2003/0120248 A1 | 6/2003 | Miyamoto |
| 2003/0135178 A1 | 7/2003 | Hansen |
| 2003/0158531 A1 | 8/2003 | Chmielewski |
| 2003/0225384 A1 | 12/2003 | Zenker et al. |
| 2004/0015142 A1 | 1/2004 | Johnston et al. |
| 2004/0020579 A1 | 2/2004 | Durrance |
| 2004/0024375 A1 | 2/2004 | Litvay |
| 2004/0054343 A1 | 3/2004 | Barnett et al. |
| 2004/0102747 A1 | 5/2004 | Bell et al. |
| 2004/0236294 A1 | 11/2004 | Drzewiecki et al. |

(56) References Cited

U.S. PATENT DOCUMENTS

| | | |
|---|---|---|
| 2004/0261231 A1 | 12/2004 | Jayshree et al. |
| 2005/0113790 A1 | 5/2005 | Minako et al. |
| 2005/0118916 A1 | 6/2005 | Ducker et al. |
| 2005/0215962 A1 | 9/2005 | Litvay et al. |
| 2006/0241557 A1 | 10/2006 | Moriya et al. |
| 2006/0265867 A1 | 11/2006 | Schaap et al. |
| 2007/0032770 A1 | 2/2007 | LaVon et al. |
| 2007/0073260 A1 | 3/2007 | Roe |
| 2007/0197897 A1 | 8/2007 | Tsang et al. |
| 2007/0197987 A1 | 8/2007 | Tsang et al. |
| 2010/0137773 A1 | 6/2010 | Gross et al. |
| 2010/0198178 A1 | 8/2010 | Litvay |
| 2010/0256584 A1 | 10/2010 | Litvay |
| 2010/0261812 A1 | 10/2010 | Qin et al. |
| 2010/0318047 A1 | 12/2010 | Ducker et al. |
| 2011/0118114 A1 | 5/2011 | Riegel |
| 2011/0162989 A1 | 7/2011 | Ducker et al. |
| 2011/0208145 A1 | 8/2011 | Zhang et al. |
| 2011/0319855 A1 | 12/2011 | Lash |
| 2012/0004632 A1 | 1/2012 | Zhang et al. |
| 2012/0035575 A1 | 2/2012 | Ehrnsperger et al. |
| 2012/0053545 A1 | 3/2012 | Love et al. |
| 2012/0143163 A1 | 6/2012 | Ng |
| 2012/0144790 A1 | 6/2012 | Cambo et al. |
| 2012/0148821 A1* | 6/2012 | Ducker .............. B32B 5/245 428/292.1 |
| 2012/0238984 A1 | 9/2012 | Paldey |
| 2012/0316526 A1 | 12/2012 | Rosati et al. |
| 2013/0046263 A1 | 2/2013 | Fukudome et al. |
| 2014/0276510 A1 | 9/2014 | Ducker et al. |
| 2014/0315034 A1 | 10/2014 | Akiyama et al. |
| 2015/0076727 A2 | 3/2015 | Rocha |
| 2015/0173959 A1 | 6/2015 | Carlucci et al. |
| 2015/0173960 A1 | 6/2015 | Mansfield |
| 2015/0230997 A1 | 8/2015 | Suzuki |
| 2015/0238369 A1 | 8/2015 | Kaiser et al. |
| 2015/0245958 A1 | 9/2015 | Chmielewski et al. |
| 2015/0257946 A1 | 9/2015 | Macura et al. |
| 2015/0320617 A1* | 11/2015 | Ducker .............. B32B 7/12 604/366 |
| 2016/0143792 A1 | 5/2016 | Peiffer |
| 2016/0220427 A1* | 8/2016 | Ducker .............. D21H 27/34 |
| 2016/0272979 A1 | 9/2016 | Roe et al. |
| 2017/0014279 A1 | 1/2017 | Bianchi et al. |
| 2017/0065466 A1 | 3/2017 | Szypka |
| 2017/0079858 A1 | 3/2017 | Willhaus et al. |
| 2017/0087034 A1 | 3/2017 | Bosser |
| 2017/0181905 A1 | 6/2017 | Sakurai |
| 2017/0258651 A1 | 9/2017 | Hammons et al. |
| 2017/0265602 A1 | 9/2017 | Rocha |
| 2017/0360628 A1 | 12/2017 | Chmielewski et al. |
| 2018/0168888 A1 | 6/2018 | Zink |
| 2018/0214319 A1 | 8/2018 | Inoue et al. |
| 2018/0243145 A1 | 8/2018 | Wright et al. |
| 2018/0338870 A1 | 11/2018 | Kreuzer |
| 2019/0328587 A1 | 10/2019 | Saevecke et al. |
| 2020/0016581 A1 | 1/2020 | Gaffney |
| 2020/0060895 A1 | 2/2020 | Chmielewski |
| 2021/0244576 A1 | 8/2021 | Albino |

FOREIGN PATENT DOCUMENTS

| | | |
|---|---|---|
| CN | 1305794 | 8/2001 |
| CN | 1323227 | 11/2001 |
| CN | 1337214 | 2/2002 |
| CN | 101868208 | 10/2010 |
| CN | 102781383 | 11/2012 |
| CN | 102970953 | 3/2013 |
| CN | 103006385 | 4/2013 |
| CN | 104780881 | 7/2015 |
| EP | 0438113 | 7/1991 |
| EP | 0556996 | 8/1993 |
| EP | 0829245 | 3/1998 |
| EP | 1027874 | 8/2000 |
| EP | 1447065 | 7/2002 |
| EP | 1245209 | 10/2002 |
| EP | 3053556 | 2/2003 |
| EP | 1519828 | 6/2003 |
| EP | 1009249 | 11/2003 |
| EP | 1272398 | 3/2004 |
| EP | 1457185 B1 | 9/2004 |
| EP | 0790884 | 12/2004 |
| EP | 1740142 | 2/2005 |
| EP | 1150585 | 7/2005 |
| EP | 1609448 | 12/2005 |
| EP | 1759606 | 3/2007 |
| EP | 1759607 | 3/2007 |
| EP | 1759608 | 3/2007 |
| EP | 1774866 | 4/2007 |
| EP | 1265507 | 1/2008 |
| EP | 2167301 | 6/2008 |
| EP | 1272139 | 7/2008 |
| EP | 2140775 | 1/2010 |
| EP | 2379308 | 1/2010 |
| EP | 2444225 | 4/2012 |
| EP | 2214525 | 5/2012 |
| EP | 2447048 | 5/2012 |
| EP | 3057752 | 10/2014 |
| EP | 3287108 | 2/2018 |
| JP | 2002085450 | 3/2002 |
| JP | 2003026701 | 1/2003 |
| JP | 2005537852 | 12/2005 |
| JP | 2012010972 | 1/2012 |
| RU | 64902 U1 | 7/2007 |
| RU | 112038 U1 | 1/2012 |
| UZ | 1258 U | 12/2017 |
| WO | WO 1995013776 | 5/1995 |
| WO | WO 1996005790 | 2/1996 |
| WO | WO 1999049826 | 10/1999 |
| WO | WO 2000/030585 | 6/2000 |
| WO | WO 2000038749 | 7/2000 |
| WO | WO 2000075427 | 12/2000 |
| WO | WO 2001/005440 | 1/2001 |
| WO | WO 2001/089439 | 11/2001 |
| WO | WO 2004/009008 | 1/2004 |
| WO | WO 2004012639 | 2/2004 |
| WO | WO 2013/126934 | 9/2013 |
| WO | WO 2013147059 | 10/2013 |
| WO | WO 2014/083501 | 6/2014 |
| WO | WO 2014144131 | 9/2014 |
| WO | WO 2015/129367 | 9/2015 |
| WO | WO 2015/171972 | 11/2015 |
| WO | WO 2016149243 | 9/2016 |
| WO | WO 2018/112229 | 6/2018 |

OTHER PUBLICATIONS

International Search Report and Written Opinion for Application No. PCT/US2020/046065, mailed Oct. 23, 2020, 16 pages.
Search Report and Written Opinion Issued in Corresponding PCT Patent Application No. PCT/US2019/064126, dated Feb. 20, 2020.
International Search Report and Written Opinion Issued in PCT Patent Application No. PCT/US2019/064136, dated Feb. 21, 2020.
Office Action issued in Corresponding Japanese Application No. 2019-531657, dated Oct. 4, 2021 (English Translation provided).
Ducker, Paul M ; Issue Notification for Parent U.S. Appl. No. 14/212,754, filed Mar. 14, 2014, mailed Dec. 29, 2015, 1 pg.
Ducker, Paul M.; Corrected Notice of Allowability for U.S. Appl. No. 14/212,754, filed Mar. 14, 2014, mailed Sep. 25, 2015, 8 pgs.
Ducker, Paul M.; Non-Final Office Action for U.S. Appl. No. 14/212,754, filed Mar. 14, 2014, mailed Jan. 14, 2015, 21 pgs.
Ducker, Paul M.; Notice of Allowance for U.S. Appl. No. 14/212,754, filed Mar. 14, 2014, mailed Aug. 17, 2015, 9 pgs.
Ducker, Paul M.; U.S. Patent Application entitled: Absorbent Structure With Discrete Acquisition Cells, having U.S. Appl. No. 14/212,754, filed Mar. 14, 2014, 30 pgs.
Ducker, Paul; U.S. Provisional Application entitled: Absorbent Structures, having U.S. Appl. No. 61/789,444, filed Mar. 15, 2013, 33pgs.
Extended European Search Report Issued in Corresponding European Application No. 16747100.2, dated Jun. 4, 2018.

(56) References Cited

OTHER PUBLICATIONS

International Preliminary Report for corresponding Application No. PCT/US2014/028292, dated Sep. 15, 2015.
International Preliminary Report for corresponding Application No. PCT/US2014/028414, dated Sep. 15, 2015.
International Search Report and Written Opinion for corresponding Application No. PCT/US2014/028292, dated Aug. 11, 2014.
International Search Report and Written Opinion for corresponding Application No. PCT/US2014/028414, dated Mar. 14, 2014.
International Search Report and Written opinion issued in International Application No. PCT/US2019/034201, dated Sep. 9, 2019.
Office Action issued in Chinese Patent Application No. 201480021203.7, dated Mar. 2, 2018.
Office Action issued in Japanese Patent Application No. 2016-502781, dated Mar. 26, 2018.
International Search Report and Written Opinion issued in corresponding application no. PCT/US2017/066467, dated Feb. 15, 2018.
Chmielewski, Harry J.; International Preliminary Report on Patentability for PCT Application No. PCT/US2014/028414, filed Sep. 15, 2015, 9 pgs.
Chmielewski, Harry J; International Search Report and Written Opinion for PCT Application No. PCT/US2014/028414, filed Mar. 14, 2014, 10 pgs.
Ducker, Paul M., International Preliminary Report for PCT Application No. PCT/US2014/028292, filed Mar. 14, 2014, mailed Sep. 15, 2015, 6 pgs.
Ducker, Paul M., International Search Report and Written Opinion for PCT Application No. PCT/US2014/028292, filed Mar. 14, 2014, mailed Aug. 11, 2014, 7 pgs.
Ducker, Paul; U.S. Provisional Application entitled: Absorbent Structures, having U.S. Appl. No. 61/789,444, filed Mar. 15, 2013.
Extended European Search Report Issued in Corresponding European Patent Application No. 18813262.5, dated Feb. 16, 2021.
International Search Report and Written Opinion issued in International Patent Application No. PCT/US2016/16142, dated Apr. 8, 2016.
International Search Report and Written Opinion Issued in International Patent Application No. PCT/US2020/015397, mailed Jul. 1, 2020.
Office Action issued in counterpart Chinese Application No. 201680011883.3, dated Mar. 3, 2020.
Decision to Grant and Search Report issued in related Russian Application No. 2020142738, dated Dec. 1, 2022 (English translation).
Extended European Search Report issued in European Application No. 15754606.0, issued Aug. 25, 2017.
International Preliminary Report on Patentability for PCT/US2015/018198 issued Sep. 15, 2016.
International Search Report and Written Opinion for Application No. PCT/US2020/042720, mailed Oct. 13, 2020.
International Search Report and Written Opinion for corresponding Application No. PCT/US2015/018198, dated Jun. 4, 2015.
International Search Report and Written Opinion for corresponding Application No. PCT/US2015/029807, dated Aug. 5, 2015.
Office Action issued in corresponding European Application No. 19828024.0 dated Apr. 12, 2024.
Office Action issued in corresponding European Application No. 19828027.3 dated Apr. 15, 2024.

\* cited by examiner

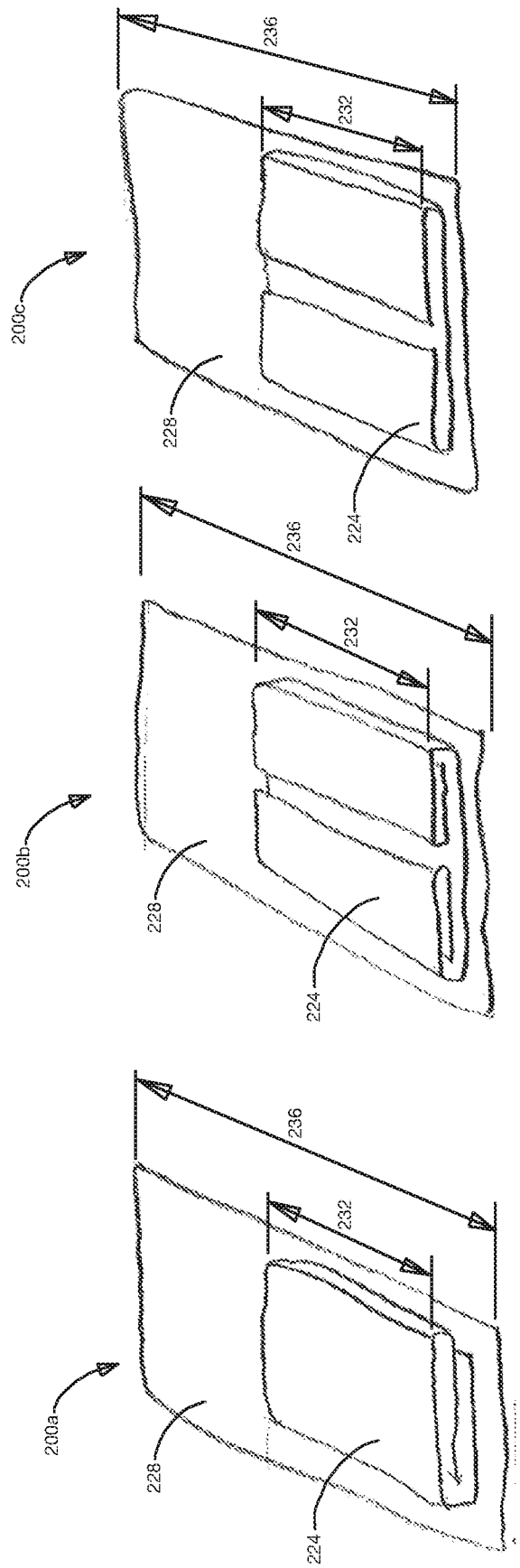

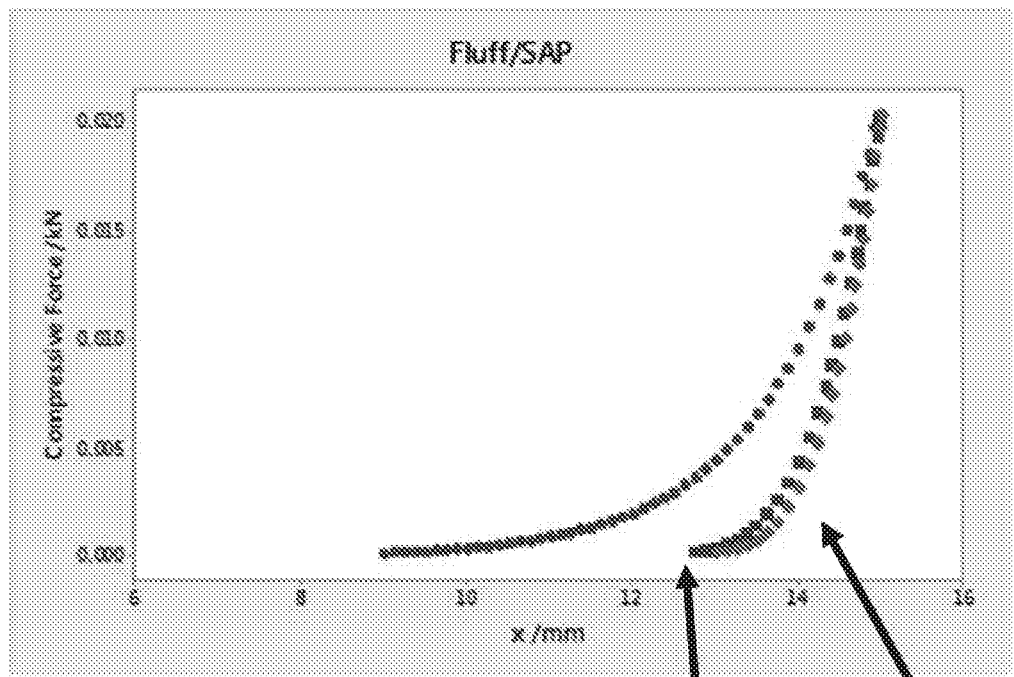
FIG. 9A 66% of thickness recovered after one cycle — stiffer after compression
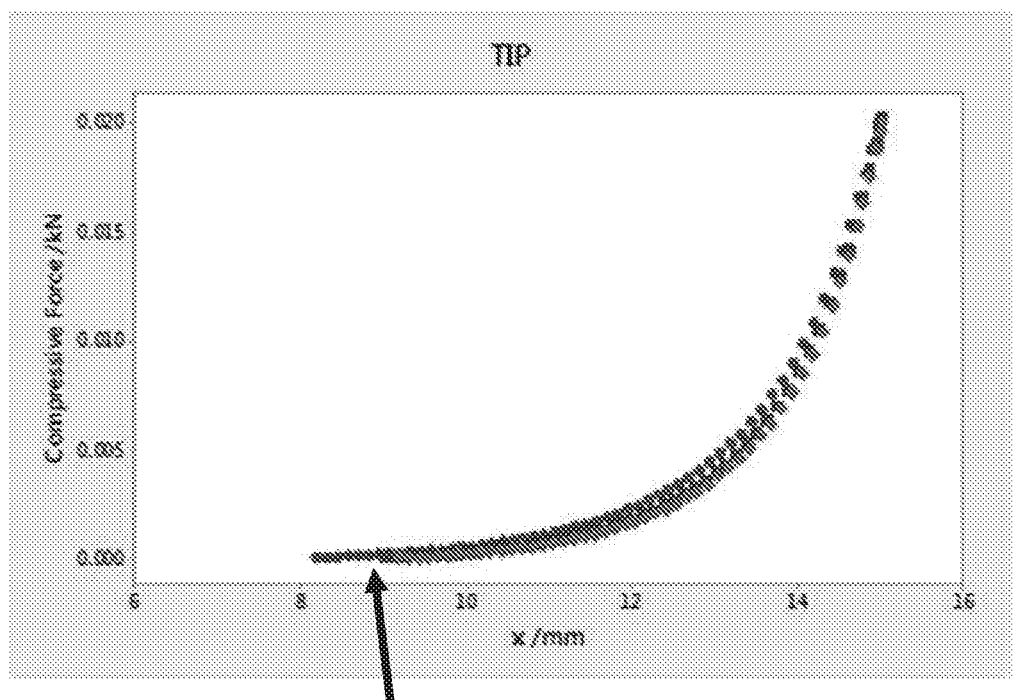
FIG. 9B 93% of thickness recovered after one cycle

ABSORBENT LAMINATES, ABSORBENT CORES AND DISPOSABLE ARTICLES UTILIZING THE ABSORBENT LAMINATES, AND RELATED METHODS

CROSS-REFERENCE TO RELATED APPLICATIONS

This application is a national phase application under 35 U.S.C. § 371 of International Application No. PCT/US2017/066467, filed Dec. 14, 2017, which claims the benefit of U.S. Provisional Application No. 62/434,156, filed Dec. 14, 2016, and U.S. Provisional Application No. 62/505,218, filed May 12, 2017, the contents of which applications are incorporated herein in their entirety.

FIELD OF INVENTION

The present invention relates generally to absorbent laminates for use in disposable absorbent products such as bed pads or underpads, adult incontinence briefs, protective pull-up underwear, and infant diapers; and more particularly, but not by way of limitation, to absorbent materials such as laminates that are more resilient than at least some prior art absorbent laminates, as well as methods of making resilient absorbent laminates and disposable articles incorporating resilient absorbent laminates for absorption of exudates from a user and/or to support the user.

BACKGROUND

Examples of disposable absorbent articles that are wearable by a user include baby diapers, training pants, and adult incontinence briefs and underwear, all of which may be made in disposable forms such as, for example, utilizing nonwoven materials. The terms "absorbent article" and "absorbent garment" refer to garments or articles that absorb and contain exudates and, more specifically, refer to garments or articles that are placed against or in proximity to the body of the wearer to absorb and contain the various exudates discharged from the body. These garments or articles, include diapers, training pants, feminine hygiene products, bibs, wound dressing, bed pads, and adult incontinence products. "Nonwoven" fabrics, according to an INDA definition, are broadly defined as sheet or web structures bonded together by entangling fiber or filaments (and by perforating films) mechanically, thermally, or chemically. They are flat, porous sheets that are made directly from separate fibers or from molten plastic or plastic film. They are not made by weaving or knitting and do not require converting the fibers to yarn. The basis weight of nonwoven fabrics is usually expressed as gsm or grams per square meter. In this context, "disposable" refers to articles which are designed to be discarded after a limited use rather than being laundered or otherwise restored for reuse. Disposable absorbent products have met with widespread acceptance in the marketplace for a variety of applications, including infant and adult incontinence care, in view of the manner in which such products can provide effective and convenient liquid absorption and retention while maintaining the comfort of the wearer.

Such disposable absorbent articles often include a topsheet that is configured to be closest to the wearer during use, a liquid-impermeable backsheet or outer cover, and an absorbent core between the topsheet and the backsheet. "Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. In some instances, such disposable absorbent articles also include an acquisition-distribution layer ("ADL") disposed between the topsheet and the absorbent core. "Absorbent core" means a structure positioned between a topsheet and backsheet of an absorbent article for absorbing and containing liquid received by the absorbent article and may comprise one or more substrates, absorbent polymer material, adhesives or other materials to bind absorbent materials in the core and, for purposes of the present invention, includes the disclosed absorbent laminate.

Examples of disposable absorbent articles that are wearable by a user include baby diapers, training pants, and adult incontinence briefs and underwear, all of which may be made in disposable forms. "Disposable" refers to articles that are designed to be discarded after a limited use rather than being laundered or otherwise restored for reuse. Disposable absorbent products have met with widespread acceptance in the marketplace for a variety of applications, including infant and adult incontinence care, in view of the manner in which such products can provide effective and convenient liquid absorption and retention while maintaining the comfort of the wearer. Such disposable absorbent articles often include a topsheet that is configured to be closest to the wearer during use, a liquid-impermeable backsheet or outer cover, and an absorbent core between the topsheet and the backsheet. In some instances, such disposable absorbent articles also include an acquisition-distribution layer (ADL) disposed between the topsheet and the absorbent core.

Disposable absorbent articles such as disposable diapers, training pants, adult incontinence articles and feminine hygiene articles are well known in the art. Such articles are designed to receive and retain bodily discharges such as urine or feces from the wearer's body.

Typically, disposable absorbent articles comprise a liquid pervious topsheet that faces the wearer's body, a liquid impervious backsheet that faces the wearer's clothing, an acquisition distribution layer underlying the liquid pervious topsheet, and an absorbent core interposed between the acquisition distribution layer and the backsheet. In operation, fluid exiting the wearer's body enters the disposable absorbent article through the topsheet and is distributed by the acquisition distribution layer for storage in the absorbent core. The backsheet prevents any excess fluid that is not absorbed from exiting the disposable absorbent article. For disposable absorbent articles like sanitary napkins intended to be worn with other clothing, the backsheet can be a garment-facing layer and typically aids in preventing soiling of the clothing. Since their introduction into the market place, disposable diapers have continued to improve regarding comfort, fit and functionalities.

U.S. Pat. No. 9,398,986 discloses certain prior art examples of training pants, and U.S. Pat. Nos. 6,976,978 and 4,940,464 disclose certain prior art examples of disposable incontinence garments or training pants.

One example of such a disposable absorbent article is shown in FIGS. 1A-1B, which depict a lower plan view and a perspective view, respectively, of adult protective underwear 10. Underwear 10 includes a chassis 14 having a front waist portion 18, an opposing rear waist portion 22, and a crotch portion 26 extending longitudinally between front and rear waist portions 18, 22. Chassis 14 further includes an outer surface 30 configured to face away from a wearer during use of the diaper, and an opposing body facing surface 34 configured to face a wearer during use of the diaper.

As shown in FIGS. 1A and 1B, underwear 10 further includes a pair of front elastic side panels 38 and a pair of rear elastic side panels 42 configured to couple rear waist portion 22 to front waist portion 18 in a well-known configuration in which a left side 46 of the chassis defines a first leg opening 50 for a wearer's left leg, and in which a right side 54 of the chassis defines a second leg opening 58 for the wearer's right leg. In the depicted configuration, each of side panels 38, 42 includes a connection portion 62 configured to be coupled to a connection portion 62 of another of side panels 38, 42. Specifically, connection portion 62 of the left one of front side panels 38 is configure to be coupled to connection portion 62 of the left one of rear side panels 42, and connection portion 62 of the right one of front side panels 38 is configure to be coupled to connection portion 62 of the right one of rear side panels 42, such that the waist portions 18, 22 and side panels, 38, 42 cooperate to define a waist opening 66 as shown in FIG. 1B. Connection portions 62 of the respective side panels can be permanently coupled together to define a tear-able side seam 70, such as, for example, via adhesive, ultrasonic, or thermal bonds. "Bonded" refers to the joining, adhering, connecting, attaching, or the like, of two elements. Two elements will be considered to be bonded together when they are bonded directly to one another or indirectly to one another, such as when each is directly bonded to intermediate elements. Such tear-able side seams generally cannot be refastened, and thereby render an article unusable once opened. Alternatively, connection portions 62 of the respective side panels can be removably coupled to define a refastenable or adjustable side seam, such as, for example, via hook-and-loop fasteners. Hook and loop fasteners are mechanical fasteners that include hooks, such as in a hook fastener portion, that are configured to engage loops in a loop fastener portion or in fibers of a sheet of fabric; for example, a nonwoven or woven fabric with fibers that define open or loop-like regions into which the hooks can extend and engage. Examples of such hook and loop fasteners may be referred to as VELCRO.

In a disposable article of the type shown in FIGS. 1A and 1B, outer surface 30 is typically defined by a water-impermeable backsheet, and body facing surface 34 is typically defined by a water-permeable topsheet. As shown in FIG. 1A, underwear 10 also includes an absorbent core 74 and an acquisition-distribution layer or "ADL" 78 disposed between the absorbent core 74 and the topsheet. "Layer" when used in the singular can be a single element or a plurality of elements. For example, a plurality of sheets may together define a single layer, such as, for example, a layer with a particular function to which the sheets of the layer contribute.

1. Absorbent Cores & Acquisition-Distribution Layers

An important component of disposable absorbent articles is the absorbent core. Conventional absorbent cores often include cellulosic fluff pulp and superabsorbent polymer or "SAP," such as hydrogel-forming polymer material. "Superabsorbent" or "superabsorbent material" or "SAP" refers to a water-swellable, water-insoluble organic or inorganic material capable, under the most favorable conditions, of absorbing at least about 15 times its weight in an aqueous solution containing 0.9 weight percent sodium chloride and, more desirably, at least about 30 times its weight in an aqueous solution containing 0.9 weight percent sodium chloride and, even more desirably, at least about 50 times its weight in an aqueous solution containing 0.9 weight percent sodium chloride. The SAP materials can be natural, synthetic and modified natural polymers and materials. In addition, the SAP materials can be inorganic materials, such as silica gels, or organic compounds such as cross linked polymers. The inclusion of SAP in an absorbent core typically increases the volume of fluid, for example urine, that can be absorbed by an absorbent core of a given volume, relative to a similarly sized core with fluff pulp alone. The inclusion of SAP in an absorbent core typically also increases the ability of the absorbent core, relative to a similarly sized absorbent core of fluff pulp alone, to retain absorbed liquid against pressure, thus providing lower rewet and better skin dryness.

Over time, absorbent cores used in such articles have become increasingly thinner with SAP being included in ever-increasing amounts in place of traditional cellulosic pulp and other fillers and absorbents. The benefits of increasing the amount of SAP and decreasing the amount of fluff pulp is that a core can be made thinner while still being able to acquire and store large quantities of discharged body fluids. Such thinner core materials can be made offline and can be introduced as a continuous web during conventional manufacturing processes. However, such thinner core designs may also have certain technical challenges or issues that often must also be addressed. One such issue is that they typically lack sufficient thickness to provide needed void volume to capture and control gushes of liquid, and typically therefore require an additional acquisition-distribution layer or "ADL" to handle fluid during insults. Another such issue is that thinner absorbent cores with predominantly SAP can have relatively low structural integrity after absorption of liquid. In some instances, relatively small quantities of thermoplastic adhesive material, such as fibrous thermoplastic adhesive material, may be included to physically stabilize the SAP. However, when the basis weight of such an absorbent core is sufficient to provide the desired absorbent performance, the relative stiffness of the absorbent core may be higher and less garment-like, particularly when adhesive or other means is included to physically stabilize the SAP. There exists an inherent conflict between relative thinness, sufficient absorbency, and wet integrity. For example, a light-strike adult incontinence product may need a core that is 25 mm wide to fit comfortably, but may as a result of the relatively small dimension need about 400 gsm of SAP to provide a desired absorbent capacity; however, such a narrow core with such a high basis weight may be difficult to provide in a stable long-running package that is suitable for commercial manufacturing lines.

While these thinner, primarily SAP-containing cores provide advantages, such as, generally offering a better fit to the wearer, they also present various challenges. One such challenge relates to the acquisition and distribution of liquid insults. In conventional core designs the liquid spreads radially from the point where it strikes, or insults, the core. Thus, rather than being dispersed across the core surface generally, its transport may be localized. This challenge is exacerbated by "gel blocking," which refers to the blocking of liquid transport through the core by the swelling and gelling of the superabsorbent material as it absorbs and retains liquid. Gel blocking may lead to leakage from the article when the core does not have the ability to absorb and retain liquid at a rate that meets or exceeds the rate at which the liquid reaches the core. To address this challenge, the properties of permeability, particularly under the applied pressure of the wearer, and capillarity are often separated between two separate structures. Conventionally, the ADL provides permeability to acquire the liquid as rapidly as it is added to the product (to prevent uncontrolled surface runoff) and then spreads or distributes the acquired liquid over a larger surface area of the absorbent core at a rate that the core can absorb the liquid without undesired internal runoff and leakage. The absorbent core, in turn, wicks the liquid into the core and provides capillary suction to reduce wetness in the ADL, to present a relatively dry ADL surface to the wearer and partially restoring the ADL to its initial state to acquire subsequent insults of liquid.

Examples of certain absorbent cores and articles that address some or all of the foregoing issues are disclosed in U.S. Patent Application Publication No. US 2015/0245958 A1, which is incorporated by reference in its entirety. This application discloses examples of absorbent laminates and folded multi-layer absorbent cores that include superabsorbent polymer particles ("SAP") and one or more layers of material such as, for example, tissue.

2. Patient-Support Articles

Non-ambulatory persons, such as those confined to beds, wheelchairs, surgical tables, and/or surgical accessory frames, often develop decubitus ulcers, frequently referred to as pressure ulcers or bed sores. Pressure ulcers can form on parts of the body where blood circulation is restricted due to elevated pressure, for example, at the interface of the person's skin and a supporting surface. The pressure at this interface may be referred to in the art as the "transdermal interface pressure" or "TIP." Pressure ulcers typically develop when TIP at a given place increases to a level that is high enough to restrict blood flow to soft tissue, and may occur most often in areas of soft tissue such as skin overlying larger bones that are relatively closer to the skin, for example, the sacrum, coccyx, heels, and hips. Such increases in TIP typically occur in soft tissue over such bones because the bone and overlying soft tissue often protrudes beyond surrounding areas of soft tissue and thus supports a relatively larger portion of the person's weight than immediately surrounding areas of soft tissue, and/or because the relatively thinner soft tissue between the bone and the skin is less effective than surrounding areas at distributing the pressure resulting from the weight of the patient. One or both of these factors can contribute to cause TIP to increase and reduce blood flow to such localized areas. For example, when a person lies on his or her back, the relatively small area of soft tissue overlying the person's heel protrudes farther than surrounding areas of tissue, such as the person's ankle, and is covered by a thinner layer of soft tissue than other parts of the person's leg, for example, the calf. As a result, the person's heel carries more of the weight of the patient's leg, over a smaller area, than surrounding areas of tissue, causing TIP under the person's heel to be higher than surrounding areas of soft tissue and potentially inhibits blood flow to the soft tissue of the person's heel.

A number of attempts have been made in the prior art to reduce the occurrence of pressure ulcers. Conventionally, patient support structures for reducing pressure ulcers can typically be considered either dynamic or static. Dynamic support structures, for example dynamically controllable pads or cushions, are those in which the properties of a support structure are dynamically varied, typically either proactively in various locations to reduce the likelihood of TIP restricting blood flow at any one point for a sufficient period of time to cause a pressure ulcer, or with sensors that indicate TIP and a feedback loop that allows a control system to respond to and reduce localized increases in TIP before a pressure ulcer arises. Although such systems may be practical for patients that are confined to a bed, they may be undesirable for patients in wheelchairs due to the difficulty in mobilizing the equipment associated with such a dynamic support structure. Dynamic support structures, such as cushions, may also be cost prohibitive for some patients due to their relatively high cost.

Static support structures, for example static pads or cushions, generally come in one of two types: (1) bladder-type cushions and (2) foam cushions. Bladder type cushions are typically flexible-walled bags, such as plastic or polymer bags, that are filled with a fluid, such as air or water, or a gel, such as ethylene glycol, polyethylene glycol, silicone, and/or the like. In contrast, foam cushions are typically solid pieces of foam or a foam laminate structure. Foam cushions are generally the less-expensive of these two types of cushion. However, foam cushions may be undesirable in that they may retain thermal energy and result in elevated temperatures at the transdermal interface between the patient's skin and the cushion, which is believed by some to be a contributing factor to the occurrence of decubitus ulcers. In contrast, bladder-type cushions tend to be more expensive, but also tend to distribute force better than foam cushions, thereby reducing TIP which is considered by many in the art to be the primary cause of pressure ulcers. Some bladder-type cushions may be low in weight and/or density like foam cushions. However, bladder-type cushions, like foam cushions, may tend to retain thermal energy and result in elevated temperatures at the transdermal interface between the patient's skin and the cushion. Another drawback with bladder-type cushions is that they tend to elevate the patient to a height greater than foam cushions.

One example of a prior art attempt to incorporate cushions into an incontinence article is disclosed in U.S. Pat. No. 4,114,621, which describes a incontinence garment for a bed-confined patient that includes "somewhat stiff pads" that overlie the patient's hips to distribute force over a greater area of the patient's soft tissue to reduce pressure ulcers.

SUMMARY

This disclosure includes embodiments of absorbent materials such as laminates that are more resilient than at least some prior art absorbent laminates, as well as methods of making resilient absorbent laminates and disposable articles incorporating resilient absorbent laminates for absorption of exudates from a user and/or to support the user. For example, some embodiments of the present absorbent materials comprise a laminate with a middle substrate layer of a nonwoven, such as a spunlace, sandwiched between two layers that each comprise an adhesive supporting the SAP particles in a porous matrix. A "matrix" as used in this disclosure is a porous structure through which fluid can travel, for example an open-celled foam, and may but need not have regular or uniform pattern of repeating substructures, for example honeycombs. When such a matrix is in a relaxed configuration in which the matrix is not under tension or compression, the relative positions of SAP particles are fixed. In some embodiments, the adhesive/SAP layers are bonded to the middle substrate layer. Some embodiments include additional outer layers of tissue or nonwoven on outer sides of the respective adhesive/SAP layers opposite the middle substrate layer; in such embodiments, the adhesive/SAP layers may be bonded to the outer layers but not to the middle substrate layer and may instead be simply folded with the middle substrate layer in a way that defines their relative positions, for example in a substantially fixed relationship.

Some embodiments of the present absorbent materials provide levels of both permeability and capillarity that are sufficient to form absorbent cores that can function without a discrete or conventional ADL. "Capillarity" refers to the tendency of a core to spread liquid away from the point of entry through the core due to surface tension—the relative attraction of the molecules of the liquid for each other and for those of the solid—even against the force of gravity. Relatively higher capillarity, for example, will typically tend to wet a greater portion or percentage of the volume of the core, and resist the drainage of liquid out of the core under the force of gravity to allow SAP in the core to more-fully absorb the liquid, for example due to the greater time of exposure between the SAP and the liquid due to such resistance to drainage. Such absorbent cores can, without a discrete or conventional ADL, acquire and store body fluids at a rate sufficient to reduce or eliminate internal runoff and leakage at a rate of fluid insult corresponding to an expected use, such as, for example, urine from an adult male or an adult female of a size for which the article is configured to be used. Some such embodiments of the present absorbent laminates also have a basis weight that is predominantly SAP but still have relatively high flexibility and physical integrity when wet. Additionally, are physically thin enough to be used to form offline absorbent cores that are, in turn, thin enough to be provided in roll form that can be unrolled at a sufficient rate for use in-line to manufacture absorbent articles. Additionally, the flexibility of the core further benefits from the fact that the individual layers of the core need not be secured—and therefore may slide—relative to one another. Further, because the present cores need not be paired with a discrete ADL, an additional ply of the absorbent laminate can instead be added in the space that an ADL would otherwise occupy and, because that additional ply is itself absorbent, it imparts an even greater absorbent capacity at the target or insult zone of the core.

Some embodiments of the present absorbent materials provide levels of physical resiliency, specifically across the thickness of a sheet or web of the material, that is sufficient to form various embodiments of patient-support articles, such as, for example, bed pads, breast pads, cushions, and disposable articles and garments that include support pads formed of the present absorbent materials that may be similar in some respects to a conventional cushion. For example, liquid can be added to one or more layers of one of the present absorbent materials in a patient-support pad to cause the SAP to swell and become more resilient than in its dry state. Once hydrated, the individual SAP particles each acts similarly to a tiny bladder, largely retaining the fluid under pressure but also resiliently deforming and interacting with adjacent SAP particles to distribute force over a larger area than it would be if the patient were supported by a hard surface and thereby reduce TIP where it is maximized and would otherwise be higher. Unlike a conventional fluff/SAP pad, the present laminates are in most instances significantly-more resilient in compression, that is, it is capable of elastic recovery from deformation in the z-direction. This can be important because a pad comprising the present laminates typically will not form bumps and ridges when it is partially hydrated. In contrast, hard bumps and ridges formed by a conventional fluff/SAP pad may be a factor in the development of a pressure ulcer. In some such embodiments of patient-support articles, the present absorbent materials can distribute force more-effectively than conventional foam cushions and, in some instances, more-effectively than conventional bladder-type cushions while also being less expensive than a bladder-type cushion.

Some such embodiments of the present patient-support articles can exhibit compressive rebound performance resulting in similar resiliency over multiple compressive cycles that may, for example, arise when a patient is repositioned on a surface over time. Alternatively or additionally, some such embodiments of the present patient-support articles may also be configured to absorb body fluids of the patient, for example, with an additional absorbent core that may also be formed of an embodiment of the present absorbent materials. Alternatively or additionally, some such embodiments of the present patient-support articles may provide improved breathability at the transdermal interface to reduce moisture at the patient's skin. Alternatively or additionally, some such embodiments of the present patient-support articles are configured to exhibit improved thermal properties, relative to conventional cushions, to reduce the temperature at the transdermal interface at the skin of a supported patient. Further, because the present absorbent materials can be configured to absorb liquid very quickly, some embodiments of the present patient-support articles can be shipped with the absorbent material in a dry state to reduce shipping charges, and a liquid such as water can be added at the point of use to increase the resiliency of the SAP.

In some instances, maximum softness and resiliency of the present materials and laminates can be obtained, for example, by pre-hydrating the material or laminate, or a product such as a pad that incorporates the material or laminate, with a quantity of fluid such as tap or distilled water or saline. For example, a product to be used in an operating room may be filled with sterile water or saline In other instances, a product incorporating one or more of the present materials or laminates can be used in any absorbent product, and its softness and resiliency will increase in situ as urine is absorbed. A product with an absorbent core of the present materials or laminates will typically remain softer and resilient that one with a fluff/SAP core over the time frame that it is worn. This performance can be advantageous for use in Adult briefs and pull up underwear, and bedpads, as well as for specialty products like breast pads for nursing mothers.

Some embodiments of the present absorbent materials are laminates. Some such laminates comprise: a first sublayer comprising super-absorbent polymer (SAP) particles and an adhesive supporting the SAP particles in a porous matrix, the SAP particles in the first sublayer having a basis weight of from 20 grams per square meter (gsm) to 130 gsm, for example, from 20 gsm to 80 gsm; a second sublayer comprising SAP particles and an adhesive supporting the SAP particles in a porous matrix, the SAP particles in the second sublayer having a basis weight of from 20 gsm to 130 gsm, for example from 20 gsm to 80 gsm; and a third sublayer disposed between, and bonded to each of, the first and second layers, the third sublayer comprising a nonwoven web of wettable cellulosic fibers, the nonwoven web having a basis weight of from 2 gsm to 80 gsm, for example from 6 gsm to 80 gsm or from 6 gsm to 50 gsm. The third sublayer can comprise a spunlace nonwoven web, for example having a basis weight of from 20 gsm to 80 gsm and/or comprising regenerated cellulosic fibers. Alternatively, the third sublayer can comprise a tissue, for example with a basis weight of from 15 gsm to 35 gsm. Some embodiments of the present absorbent laminates further comprise: a fourth sublayer bonded to the first sublayer such that the first sublayer is disposed between the fourth sublayer and the third sublayer, the fourth sublayer comprising tissue; and a fifth sublayer bonded to the second sublayer such that the second sublayer is disposed between the fifth sublayer and the third sublayer, the fifth sublayer comprising tissue. The tissue of the fourth sublayer and/or of fifth sublayers can be creped and/or through-air dried. Additionally or alternatively, a thickness of the second sublayer can be equal to a thickness of the first sublayer, and/or the basis weight of the SAP particles in the second sublayer can be equal to the basis weight of the SAP particles in the first sublayer. Additionally or alternatively, a basis weight of the adhesive in the first sublayer can be from 0.5 to 5 gsm, and a basis weight of the adhesive in the second sublayer can be from 0.5 to 5 gsm.

Some embodiments of the present absorbent laminates have a caliper of less than 1.3 millimeters (mm). Some embodiments of the present laminates have a tensile strength in at least one direction of at least 40 Newtons per 50 mm (N/50 mm).

In some embodiments of the present absorbent cores for disposable absorbent articles, the absorbent core comprises: one or more pieces of an embodiment of the present absorbent laminates, with the one or more pieces of absorbent laminate defining a plurality of layers of the absorbent laminate. For example, a single piece of the absorbent laminate can be folded to define the plurality of layers of the absorbent laminate, or multiple pieces of the absorbent laminate are stacked to define the multiple layers of the absorbent laminate. Some embodiments of the present absorbent cores further comprise: an additional piece of an embodiment of the present absorbent laminates coupled to an upper outermost one of the sublayers of the absorbent laminate. For example, the plurality of layers of the absorbent laminate have a combined width and a combined length that is greater than the combined width, the combined length extending from a first end to a second end of the absorbent core, and if the additional piece has a length that is shorter than the combined length, and the additional piece can be disposed closer to the first end of the plurality of layers than to the second end of the plurality of layers. In some cores, the combined length of the plurality of layers of the absorbent laminate is from 50% to 70% of the length of the additional piece of the absorbent laminate. In some cores, the plurality of the layers of the absorbent laminate are defined by a first piece of the absorbent laminate that is folded, and the additional piece of the absorbent laminate is not folded. Some embodiments of the present cores are configured to exhibit a resiliency greater than 70% when partially hydrated. Some embodiments of the present cores are configured to exhibit a Stress-Based Softness for a second compression cycle, at a pressure of $5\times10^3$ Pa, of less than $150\times10^3$ Pa when a 100 mm×100 mm section of the absorbent core is dosed with 145 milliliters (mL) of water. Some embodiments of the present cores are configured to exhibit a Strain-Based Softness for a second compression cycle, at a strain of 10%, of less than $4\times10^{-3}$ Pa when a 100 mm×100 mm section of the absorbent core is dosed with 100 milliliters (mL) of water.

Some embodiments of the present disposable absorbent articles comprise: a liquid-permeable topsheet; a liquid-impermeable backsheet; and an embodiment of the present absorbent cores disposed between the topsheet and the backsheet. Such absorbent articles may, for example, omit or otherwise not include an acquisition-distribution layer in addition to the absorbent core. By way of example, such an absorbent article can be a bed pad, and the absorbent core can have a width of at least 12 inches and a length of at least 18 inches.

In some embodiments of the present methods of making an absorbent laminate, the method can comprise: distributing adhesive and super-absorbent polymer (SAP) particles on a first side of a nonwoven web of wettable cellulosic fibers defining a first sublayer such that the adhesive supports the SAP particles in a porous matrix to define a second sublayer, the nonwoven web having a basis weight of from 6 grams per square meter (gsm) to 80 gsm, the SAP particles in the second sublayer having a basis weight of from 20 gsm to 80 gsm; and distributing adhesive and super-absorbent polymer (SAP) particles on a second side of a nonwoven web of wettable cellulosic fibers such that the adhesive supports the SAP particles in a porous matrix to define a third sublayer, the SAP particles in the third sublayer having a basis weight of from 20 gsm to 80 gsm. Some embodiments further comprise: while the adhesive of the first sublayer is tacky, applying a fourth sublayer to the first sublayer such that the fourth sublayer bonds to the first sublayer with the first sublayer disposed between the fourth sublayer and the third sublayer, the fourth sublayer comprising tissue; and while the adhesive of the second sublayer is tacky, applying a fifth sublayer to the second sublayer such that the fifth sublayer bonds to the second sublayer with the second sublayer disposed between the fifth sublayer and the third sublayer, the fifth sublayer comprising tissue.

In some embodiments of the present methods of making an absorbent core for disposable absorbent articles, the method comprises: stacking a plurality of layers of an embodiment of the present absorbent laminates. For example, the plurality of layers can be stacked by folding a single piece of the absorbent laminate over itself.

Some embodiments of the present disposable patient-support articles comprise: a support core comprising one or more pieces of an embodiment of the present absorbent laminates with the one or more pieces defining define a plurality of layers of the absorbent laminate; and a liquid impermeable layer coupled to the support core. For example, a single piece of the absorbent laminate can be folded to define the plurality of layers of the absorbent laminate, or multiple pieces of the absorbent laminate are stacked to define the multiple layers of the absorbent laminate. Some embodiments of the present support cores further comprise: an additional piece of an embodiment of the present absorbent laminates coupled to an upper outermost one of the sublayers of the absorbent laminate. For example, the plurality of layers of the absorbent laminate have a combined width and a combined length that is greater than the combined width, the combined length extending from a first end to a second end of the absorbent core, and if the additional piece has a length that is shorter than the combined length, and the additional piece can be disposed closer to the first end of the plurality of layers than to the second end of the plurality of layers. In some embodiments, the support core can have a width of at least 8 inches and a length of at least 8 inches. In some embodiments of the present patient-support articles, the support core is a first support core and the patient-support article further comprises: a second support core comprising one or more second pieces of an embodiment of the present absorbent laminates with the one or more second pieces defining a plurality of layers of the absorbent laminate, and the second support core is coupled to the liquid impermeable layer and laterally spaced from the first support core.

In some embodiments of the present patient-support articles, the liquid-impermeable layer is a backsheet, and the patient-support article further comprises: a topsheet; where the support core is disposed between the backsheet and the topsheet such that the backsheet and topsheet form an enclosure in which the support core is disposed. The topsheet may be liquid-permeable, for example a hydrophilic nonwoven or apertured film, or may be liquid-impermeable, for example, a polymer film that is a resilient and three-dimensional. In some configurations, the topsheet is vapor-permeable.

In some embodiments of the present patient-support articles, the patient-support pad is configured to permit liquid to be delivered to the SAP particles prior to positioning the patient-support pad under a patient. For example, the liquid-impermeable layer can define an enclosure in which the support core is disposed, and the patient-support pad can further comprise: an inlet through which liquid can be introduced into the enclosure. Alternatively, the liquid-impermeable layer can define an enclosure in which the support core is disposed, and the patient-support pad can further comprise: a container holding a volume of liquid sufficient to, when absorbed by the SAP particles, swell at least a portion of the SAP particles to at least a desired resiliency; where the container is disposed in the enclosure and configured to be ruptured to release the liquid within in the enclosure.

In some embodiments of the present patient-support articles, the backsheet and topsheet cooperate to define at least a portion of a pair of adult protective underwear. For example, the protective underwear is configured such that when worn by a user the support core is aligned with at least a portion of one of the wearer's hips. In other embodiments of the present patient-support articles, the backsheet and topsheet cooperate to define at least a portion of a chassis of a bed pad. In other embodiments of the present patient-support articles, the backsheet and topsheet cooperate to define at least a portion of: a pad that is configured to be coupled to an absorbent article, a pad having a dermal adhesive configured to adhere the pad directly to a patient's skin, and/or a pad that is shaped or contoured to overlie a portion of a human body such as a patient's heel. In yet further embodiments of the present patient-support articles, the backsheet and topsheet cooperate to define at least a portion of a chassis of a seat cushion.

Some embodiments of the present methods comprise: delivering liquid to the support core of an embodiment of the present disposable patient-support articles; allowing the support core to absorb a sufficient volume of the liquid to increase the resilience in compression of the support core; and disposing, after the liquid has been delivered to the support core, the patient-support article between at least a portion of a patient and a surface supporting the at least a portion of the patient.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the term "substantially" may be substituted with "within [a percentage] of" what is specified, where the percentage includes 0.1, 1, 5, and 10 percent.

The terms "comprise" and any form thereof such as "comprises" and "comprising," "have" and any form thereof such as "has" and "having," and "include" and any form thereof such as "includes" and "including" are open-ended linking verbs. As a result, an apparatus that "comprises," "has," or "includes" one or more elements possesses those one or more elements, but is not limited to possessing only those elements. Likewise, a method that "comprises," "has," or "includes" one or more steps possesses those one or more steps, but is not limited to possessing only those one or more steps.

Any embodiment of any of the present materials, laminates, articles, and methods can consist of or consist essentially of—rather than comprise/include/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Further, a material, laminate, or article that is configured in a certain way is configured in at least that way, but it can also be configured in other ways than those specifically described.

The feature or features of one embodiment may be applied to other embodiments, even though not described or illustrated, unless expressly prohibited by this disclosure or the nature of the embodiments.

Some details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

FIGS. 8A-8C depict alternate configurations of the present folded cores.

FIGS. 9A and 9B depict compression properties of a traditional fluff/SAP core and the core of FIG. 5, respectively, over several compression cycles after absorbing fluid.

DETAILED DESCRIPTION OF ILLUSTRATIVE EMBODIMENTS

Figure 1A:
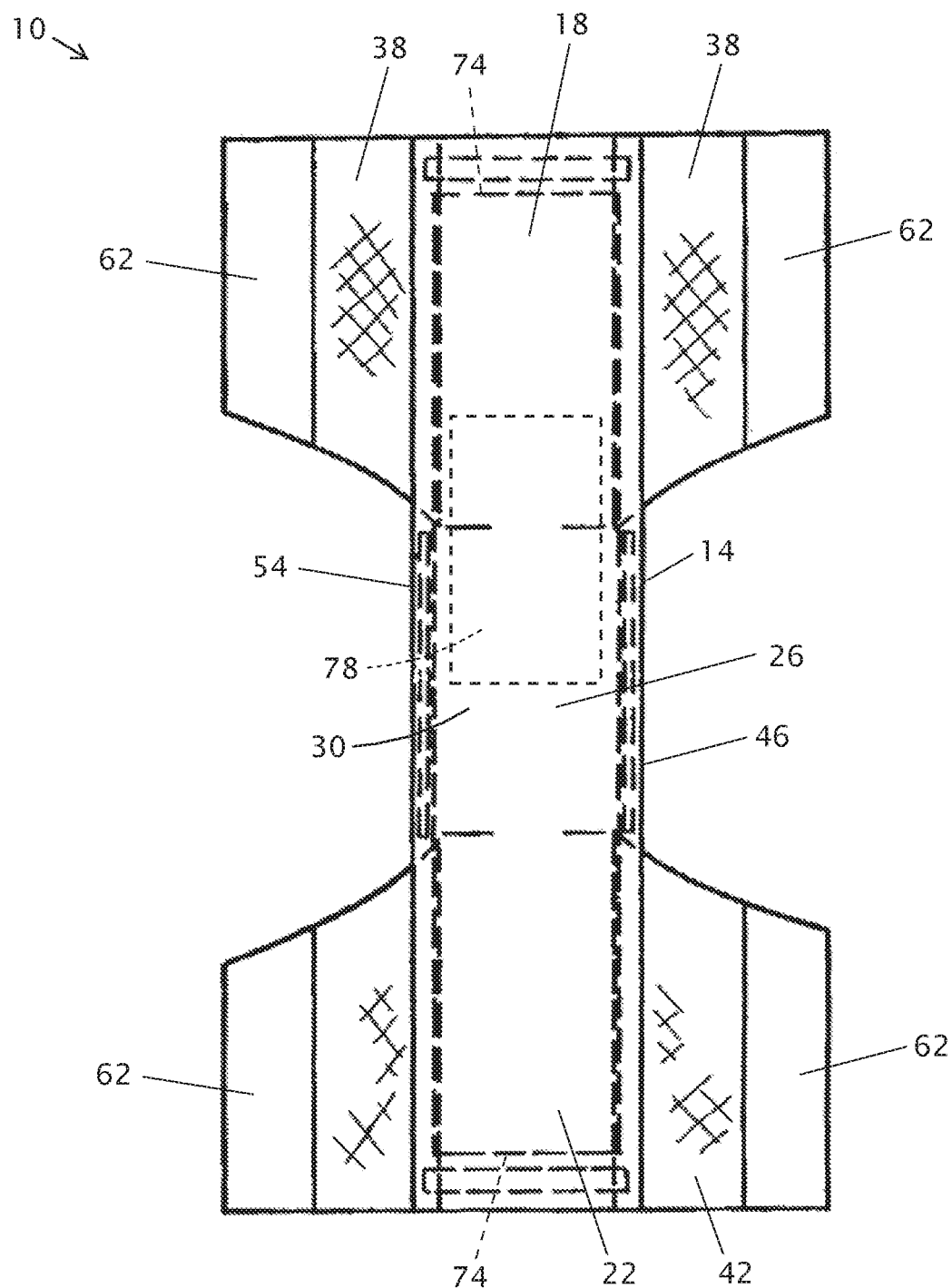
FIG. 1A depicts a bottom plan view of a prior art disposable absorbent article, specifically adult protective underwear, in an open configuration.
Figure 1B:
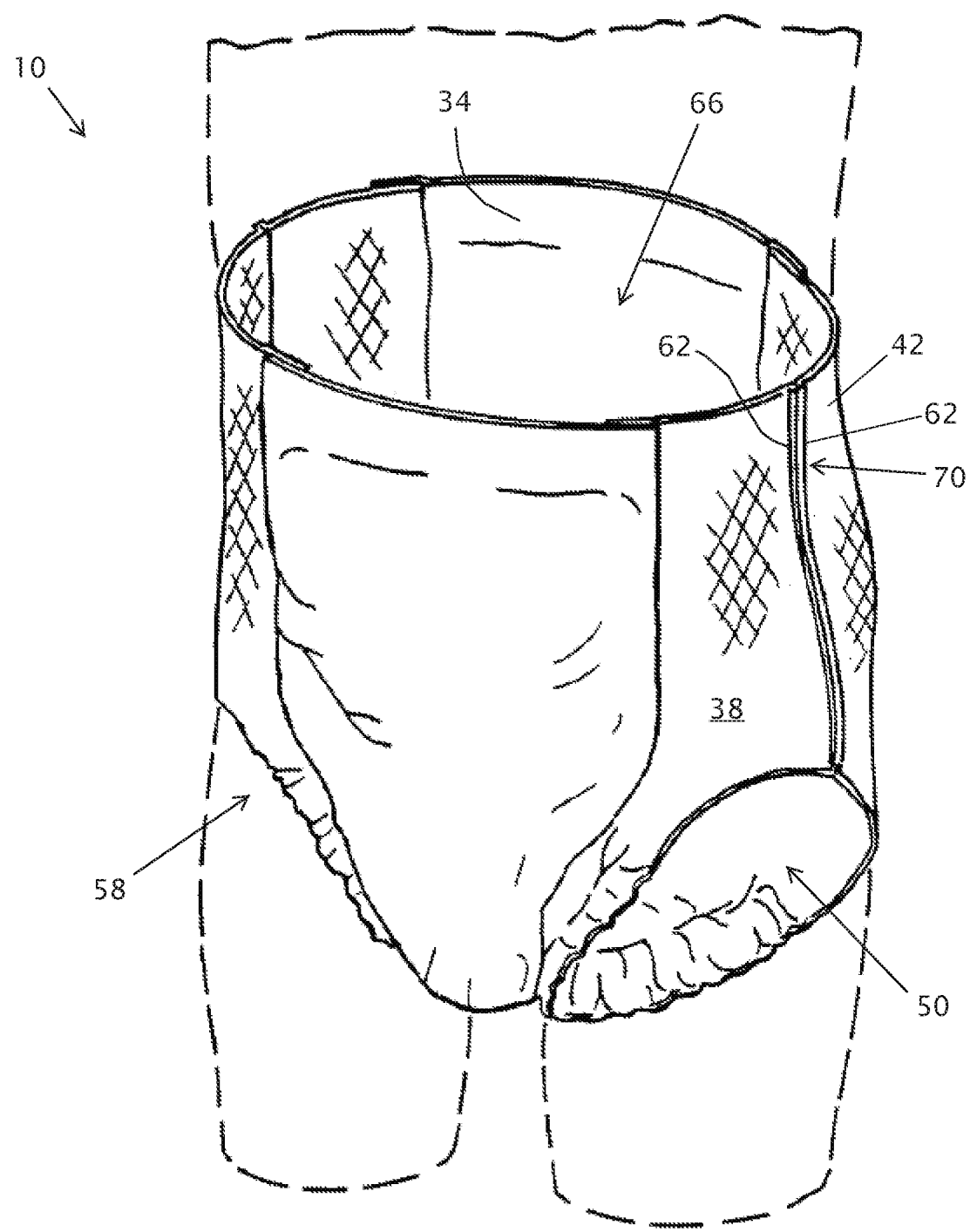
FIG. 1B depicts a perspective view of the protective underwear of FIG. 1A in a closed configuration.
Figure 2:
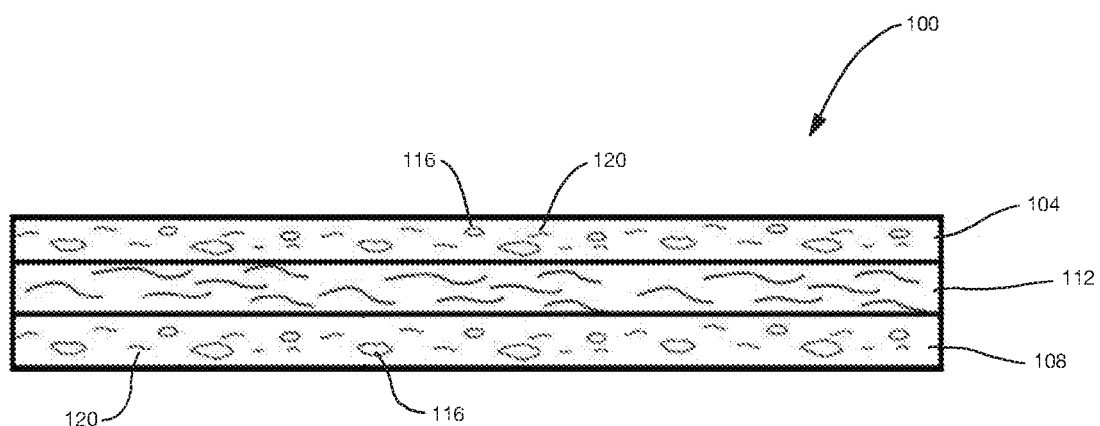
FIG. 2 depicts a schematic cross-sectional view of a first embodiment of an absorbent laminate.

Referring now to FIG. 2, shown there and designated by the reference numeral 100 is a first embodiment of an absorbent material. As shown, material 100 is a laminate that comprises a first sublayer 104, a second sublayer 108, and a third sublayer 112 disposed between the first and second sublayers. Third sublayer provide a middle substrate for the first and second sublayers 104, 108, which are more absorbent than third sublayer 112. As shown, the sublayers are arranged such that a lower side of first sublayer 104 contacts an upper side of third sublayer 112, and an upper side of second sublayer 108 contacts a lower side of third sublayer 112. In the embodiment shown, each of the sublayers 104, 108, 112 has a substantially uniform thickness across its respective area; in other embodiments, the respective thicknesses of the sublayers may vary. In some embodiments, each of first, second, and third sublayers 104, 108, 112 have similar thicknesses.

In the embodiment shown, the middle substrate sublayer, i.e., third sublayer 112, comprises a nonwoven web, for example a spunlace nonwoven. By way of example, the middle substrate sublayer, i.e., third sublayer 112, can comprise wettable, regenerated cellulosic fibers such as, for example, viscose or Tencel®. The middle substrate sublayer, i.e., third sublayer 112, can have a basis weight of from 2 grams per square meter (gsm) to 80 gsm, for example from 10 gsm to 30 gsm, from 17 gsm to 23 gsm, equal to 20 gsm, or equal to 30 gsm. By way of example, the middle substrate layer can utilize a web of spunlace viscose fibers have a basis weight of from 20 gsm to 80 gsm, for example 20 gsm or 30 gsm; or can utilize a web of spunbond viscose fibers having a basis weight of from 6 gsm to 40 gsm. In other embodiments, the middle substrate layer, i.e., third sublayer 112, can comprise a through-air-dried (TAD) tissue with a basis weight of from 10 gsm to 35 gsm, for example, from 15 gsm to 30 gsm, from 18 gsm to 28 gsm, or equal to 19 gsm. In yet further embodiments, the middle substrate layer, i.e., third sublayer 112, can comprise wettable TAD or resin-bonded, carded polyester nonwovens, for example, of the types typically used as acquisition distribution layers in absorbent products.

Each of the absorbent sublayers (first and second sublayers 104, 108) comprises super-absorbent polymer (SAP) particles 116 and an adhesive 120 supporting the SAP particles in a porous matrix. In addition to permitting fluid to travel through the absorbent sublayers, the porous matrix also improves the compressibility and resilience of the laminate even when the SAP particles are dry. The SAP particles in each of the absorbent sublayers (first and second sublayers 104, 108) has a basis weight of from 20 gsm to 80 gsm, for example from 35 gsm to 65 gsm, from 45 gsm to 55 gsm, or equal to 50 gsm. The adhesive in each of the absorbent sublayers (first and second sublayers 104, 108) can have a basis weight of from 0.5 gsm to 10 gsm, for example from 0.5 gsm to 5 gsm, from 1 gsm to 3 gsm, or equal to 2 gsm. The adhesive basis weight may also be expressed as a percentage of the SAP basis weight; for example, the basis weight of the adhesive may be from 2% to 6% of the basis weight of the SAP particles.

In the embodiment shown, first sublayer 104 is similar to second sublayer 108, including in SAP basis weight and thickness; however, in other embodiments, second sublayer 108 may differ from first sublayer 104 in any of various properties such as SAP basis weight, thickness, and/or the like. In one example, first sublayer 104 can have SAP basis weight of 40 gsm and an adhesive basis weight of 1.5 gsm, while second sublayer 108 can have a SAP basis weight of 60 gsm and an adhesive basis weight of 2.5 gsm. The adhesive (120) can be configured to provide adhesion while concurrently being permeable to liquids in order to allow the liquids to pass into and/or through the absorbent sublayers (first and second sublayers 104, 108). For example, the adhesive can be included in the absorbent sublayers in sufficient quantity to cause absorbent laminate 10 to exhibit minimum structural properties, for example, an elongation at break of at least 100%, for example from 600% to 1800%, to reduce gel blocking when the SAP are swollen by body fluids.

As mentioned, the SAP material can be in the form of particles 116. Exemplary superabsorbent polymer material can comprise any superabsorbent polymer particles known from superabsorbent literature, for example such as described in Modern Superabsorbent Polymer Technology, F. L. Buchholz, A. T. Graham, Wiley 1998. For example, the SAP particles may be spherical, spherical-like or irregularly shaped particles, such as sausage shaped particles, or ellipsoid shaped particles of the kind typically obtained from inverse phase suspension polymerizations. The SAP particles can also be optionally agglomerated at least to some extent to form larger irregular particles. In some embodiments, the SAP particles 116 can also have a surface modification, such as a partial or full surface coating, for example to increase the hydrophilicity of the SAP particles.

The SAP particles can comprise any of a variety of materials or combinations thereof, including organic compounds, such as cross-linked polymers. "Cross-linked" is a commonly understood term and refers to any approach for effectively rendering normally water-soluble materials substantially water insoluble, but swellable. Such polymers can include, for example, carboxymethylcellulose, alkali metal salts of polyacrylic acids, polyacrylamides, polyvinyl ethers, hydroxypropyl cellulose, polyvinyl morpholinone, polymers and copolymers of vinyl sulfonic acid, polyacrylates, polyacrylamides, polyvinyl pyridine and the like. Other suitable polymers include hydrolyzed acrylonitrile grafted starch, acrylic acid grafted starch, and isobutylene maleic anhydride copolymers, and mixtures thereof. Organic high-absorbency materials can include natural materials, such as agar, pectin, guar gum and peat moss. In addition to organic materials, superabsorbent materials may also include inorganic materials, such as absorbent clays and silica gels. Suitable examples of SAP include T9030, T9600, T9900, and Saviva polymers from BASF Corporation in Charlotte, North Carolina; and W211, W112A, W125, S125D, QX-W1482, QX-W1486, QX-W1504, and QX-W1505 from Nippon Shokubai Co. Ltd, N.A.I.I. in Houston, Texas; and AQUA KEEP SA50 II, SA55SX II, SA60N II, SA65S, HP500, HP500E, HP600, HP600E, and HP700E from Sumitomo Seika Chemicals Co., Ltd. in Osaka, Japan.

SAP particles 116 can have a particle size distribution in the range typical of SAP commercially used in disposable hygiene products. In some embodiments, the SAP particles have sizes between about 45 micrometers (µm) and 4000 µm, for example between 45 µm and 2000 µm, or from 100 µm to 1000 µm. The particle size distribution of a material in particulate form can be determined, for example, by means of dry sieve analysis (EDANA 420.02 Particle Size distribution). In some embodiments, at least 90%—for example at least 95% or at least 98%—of the SAP particles have a particle size diameter ranging from 45 to 850 µm, for example from 100 µm to 800 µm or from 200 µm to 500 µm. Surface roughness of the present laminates pad may be reduced, in some instances greatly, when less than 2% of the mass of the SAP particles is provided by particles sized greater than 500 µm. Surface roughness may also be reduced when outer layers 104, 108 comprised TAD tissue, for example TAD tissue with a basis weight of from 18 to 20 gsm.

In some embodiments, the absorbent laminate as a whole and/or the SAP particles, can have a relatively high sorption capacity, i.e., can have a centrifuge retention capacity or "CRC" tested in 0.9% saline of at least 20 grams of saline per gram of material (g/g), or at least 30 g/g. In some embodiments, the CRC may be as high as 45 g/g or 50 g/g.

In the embodiment shown, each of first and second sublayers 104, 108 is bonded to third sublayer 112. In other embodiments, first and second sublayers 104, 108 need not be bonded to third sublayer; for example, as an alternative to a laminate configuration, first and second sublayers may be independently formed and stacked with third sublayer 112 in the depicted configuration but without bonding, and the sublayers folded together, as discussed below with reference to FIGS. 7A and 7B, such that the folds rather than bonds maintain the relative positions of the sublayers.

Figure 3:
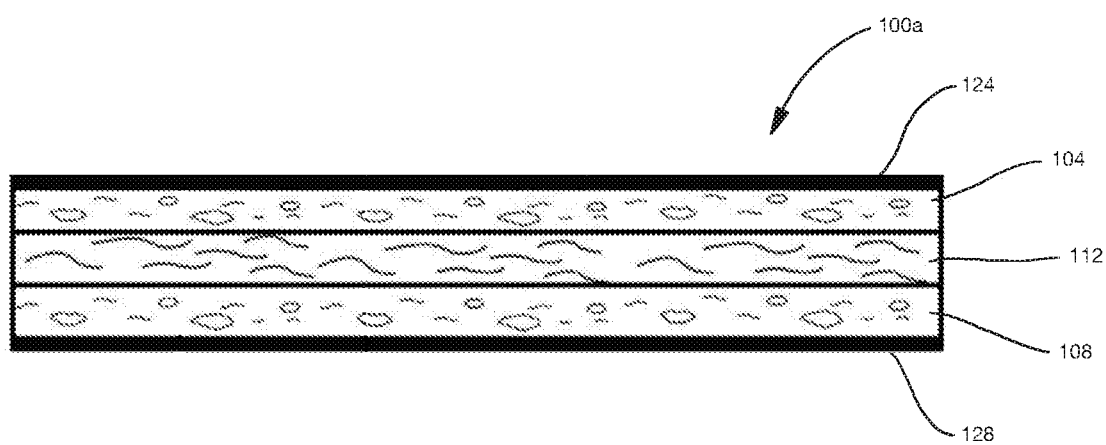
FIG. 3 depicts a schematic cross-sectional view of a second embodiment of an absorbent laminate.

FIG. 3 depicts a second embodiment 100a of an absorbent laminate. Absorbent laminate 100a is substantially similar to absorbent laminate 100, with the exception that absorbent laminate 100a includes additional outer layers. As such, the difference will primary be described here, and it should be understood that those components of laminate 100a not labeled in FIG. 3 or described here are substantially similar to the components of laminate 100. As shown in FIG. 3, laminate 100a includes a fourth sublayer 124 and a fifth sublayer 128. Fourth sublayer 124 is bonded to first sublayer 104 such that first sublayer 104 is disposed between fourth sublayer 124 and third sublayer 112, and fifth sublayer 128 is bonded to second sublayer 108 such that second sublayer 108 is disposed between fifth sublayer 128 and third sublayer 112. In this embodiment, each of the outer sublayers, i.e., fourth and fifth sublayers 124, 128, comprises tissue with sufficient porosity to permit fluid to travel through the tissue into the absorbent sublayers, for example, a creped or through-air dried tissue. The tissue can have a basis weight of from 10 gsm to 25 gsm, for example from 15 gsm to 20 gsm, or equal to 17 gsm. One example of a tissue suitable in at least some embodiments for the outer layers, i.e., fourth and fifth sublayers, is a 17-gsm 3995 Machine Creped tissue from Dunn paper. In other embodiments, each of the outer sublayers, i.e., fourth and fifth sublayers 124, 128, comprises a nonwoven. In one example of a material having the configuration of FIG. 3, first sublayer 104 comprises a spunlace nonwoven of viscose fibers with a basis weight of 20 gsm, each of second and third sublayers 108, 112 comprises 50 gsm of BASF T9900 SAP particles and 2 gsm of Savare E60W adhesive, and each of fourth and fifth sublayers 124, 128 comprises a 17 gsm 3995 machine creped tissue from Dunn paper, such that the overall laminate is highly flexible and has a basis weight of 158 gsm and is thinner than 1.5 millimeters (mm).

In some embodiments, the outer sublayers, i.e., fourth and fifth sublayers 124, 128, can comprise TAD tissue, standard tissue, spunbond synthetic nonwoven, carded synthetic nonwoven, or apertured film. For example, in one example, fourth sublayer 124 comprises a TAD tissue, fifth sublayer 128 comprises a standard tissue, and third sublayer 112 comprises a spunlace nonwoven or a TAD tissue. In yet further embodiments, laminate 10a may comprise additional inner substrate layers and SAP/adhesive layers. For example, laminate 10 can in some instances comprise two or more third sublayers 112 of spunlace or TAD tissue with a corresponding number of SAP/adhesive sublayers, similar for example to sublayers 104, 108.

In the embodiment of FIG. 3, the basis weight of SAP in sublayers 104 and 108 can be selected for a particular core configuration. For example, sublayers 104 and 108 can each include 50 gsm, 75 gsm, 100 gsm, or 150 gsm of SAP. Once the basis weight of SAP in each of sublayers 104 and 108 is known, the number of layers of laminate can then be selected to achieve a desired overall basis weight of SAP in an absorbent core. By way of example, when a total basis weight of SAP of 300 gsm is desired, three layers can be used of laminate with a total of 100 gsm SAP—50 gsm of SAP in each of sublayers 104, 108; two layers can be used of a laminate with a total of 150 gsm SAP—75 gsm of SAP in each of sublayers 104, 108; or one layer can be used of a laminate with a total of 300 gsm of SAP—150 gsm of SAP in each of sublayers 104, 108. If instead a total basis weight of SAP of 200 gsm is desired, two layers can be used of a laminate with a total of 100 gsm SAP—50 gsm of SAP in each of sublayers 104, 108; or one layer can be used of a laminate with a total of 200 gsm of SAP—100 gsm of SAP in each of sublayers 104, 108. Qualitative observation of partially hydrated TIP cores suggests that the resiliency and softness decreases as the basis weight of an individual SAP layer in a laminate increases, and as the number of layers of absorbent laminate in a core decreases.

Figure 4A:
FIGS. 4A-4C depict stages of a method of manufacturing the laminate of FIG. 2.
Figure 4B:
Figure 4C:
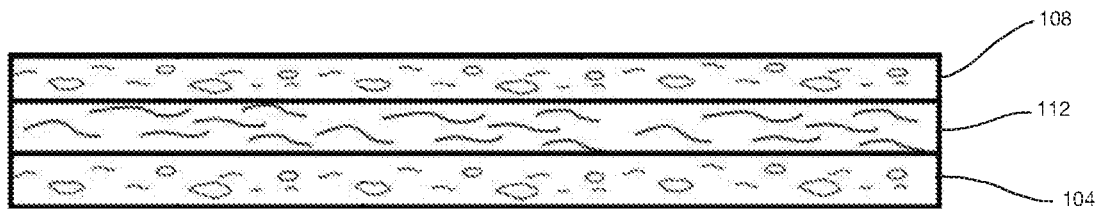

FIGS. 4A-4C depict stages of a method of manufacturing laminate 100 of FIG. 2. As shown in FIG. 4A, the process begins with the middle substrate sublayer, i.e., third sublayer 112.

As shown in FIG. 4B, first sublayer 104 is added to a first side of third sublayer 112. For example, adding first sublayer 104 can include distributing adhesive, for example by spraying, on the first side of third sublayer 112, and airlaying super-absorbent polymer (SAP) particles in contact with the adhesive on the first side of third sublayer 112 to define first sublayer 104. The adhesive on the first side of third sublayer 112 can, for example, comprise a foam. In some embodiments, the adhesive and SAP of each sublayer are applied as a mixture to the nonwoven web.

As shown in FIG. 4C, second sublayer 108 is added to a second side of third sublayer 112. For example, adding second sublayer 108 can include distributing adhesive, for example by spraying, on the second side of third sublayer 112, and airlaying super-absorbent polymer (SAP) particles in contact with the adhesive on the first side of third sublayer 112 to define second sublayer 108. The adhesive on the second side of third sublayer 112 can, for example, comprise a foam. As shown in FIG. 4C, because the SAP particles are airlaid in this embodiment, third sublayer 112 is turned over so that the second side of the third sublayer (112) is facing up to receive the adhesive and SAP particles. In some embodiments, the adhesive and SAP of each sublayer are applied as a mixture to the nonwoven web.

In the present methods of making laminate 100, the SAP particles can be conventionally mixed with hot melt adhesive fibers of the type produced by commercially available meltblown-type glue heads widely used in the manufacture of disposable absorbent articles. The hot melt adhesive can be any adhesive, for example a pressure sensitive adhesive, suitable for use in the high speed manufacture of disposable absorbent articles, with the necessary rheology to form glue fibers in the commercially available meltblown systems. In one aspect, the hot melt adhesive can be a tacky pressure sensitive synthetic rubber based adhesive, such as, for example and without limitation, Styrene-Butadiene-Styrene (SBS) or Styrene-Isoprene-Styrene (SIS) block copolymer based adhesive types. Such hot melt adhesive fibers can be added in quantities necessary to produce materials that have lamination strengths strong enough to sustain the mechanical forces applied during converting, but not excessive amounts that would interfere with the swelling of the SAP particles. In some embodiments, the adhesive has a glass transition temperature that is higher than room temperature, i.e., 73 degrees, to maintain stability while retaining flexibility. Examples of a suitable, commercially available adhesive is HB Fuller NW 1023 AAZP and Savare E60W. In some embodiments, each absorbent sublayer, i.e., first and second sublayers 104, 108, is formed by sequentially distributing adhesive, airlaying SAP particles, distributing adhesive, and airlaying SAP particles in multiple steps to build up the respective absorbent sublayer.

Figure 4D:
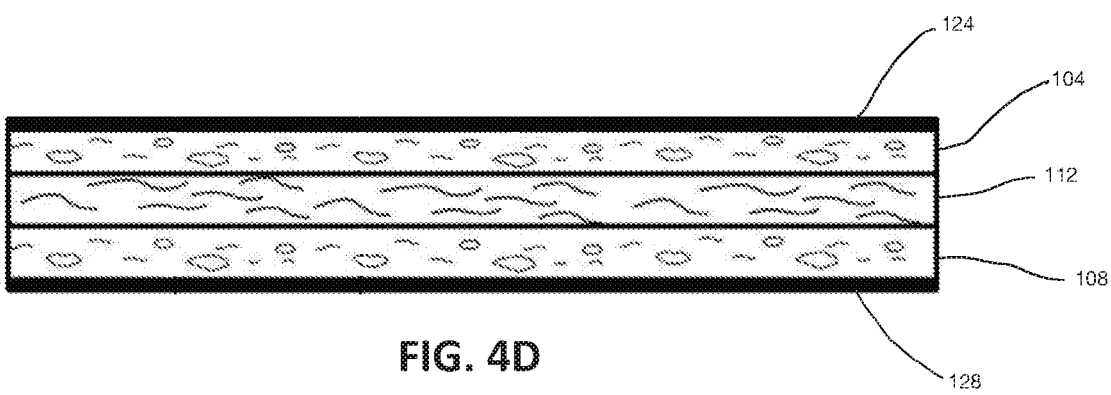
FIG. 4D depicts a further stage of a method of manufacturing the laminate of FIG. 3.

FIG. 4D depicts a further stage of a method of manufacturing laminate 100a of FIG. 3. As shown, the outer sublayers, i.e., fourth and fifth sublayers 124, 128, are added to the outer sides of the respective absorbent sublayers, i.e., first and second sublayers 104, 108. In some embodiments, the tissue is added and pressure applied to adhere the tissue to the respective absorbent sublayer, i.e., first or second sublayer 104, 108, before the adhesive of that sublayer is fully cooled. In other embodiments, the adhesive is distributed and SAP particles airlaid onto a respective tissue sublayer, i.e., fourth or fifth sublayer 124, 128, and the combined tissue sublayer and absorbent sublayer are subsequently positioned relative to the middle substrate layer, i.e., third sublayer 112.

Figure 5:
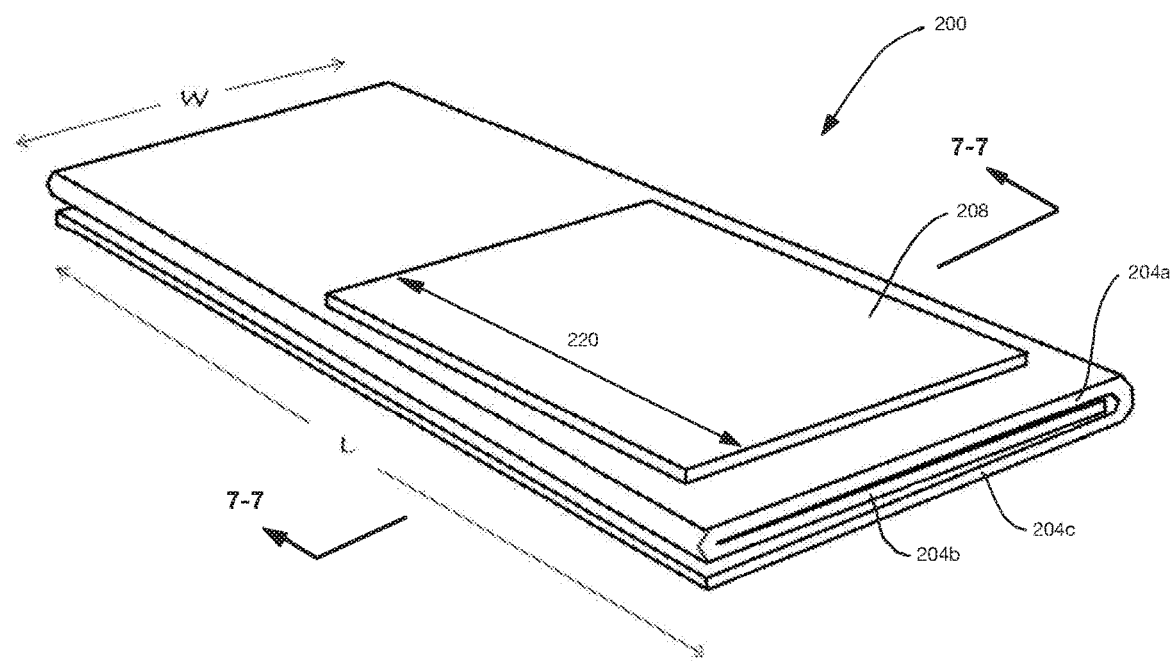
FIG. 5 depicts a perspective view of an embodiment of a core utilizing an embodiment of the present absorbent laminates.
Figure 6:
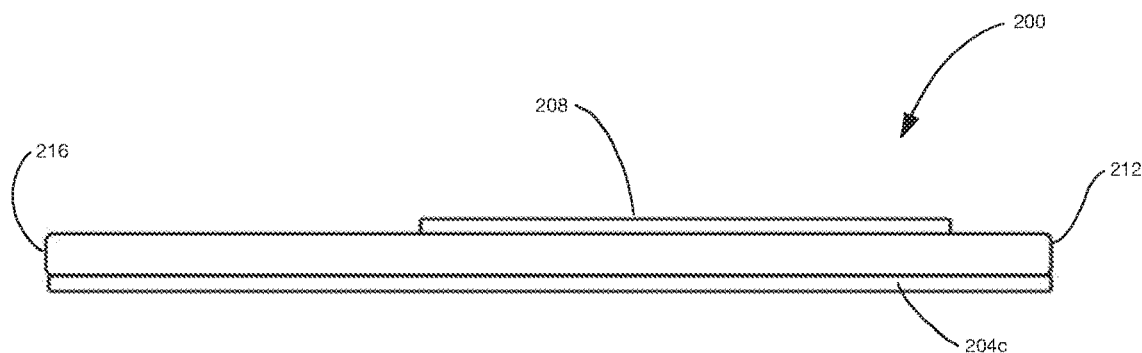
FIG. 6 depicts a side view of the core of FIG. 4.

Referring now to FIGS. 5 and 6; FIG. 5 depicts a perspective view of an embodiment of a core 200 utilizing an embodiment of the present absorbent laminates, for example laminate 100 or laminate 100a; and FIG. 6 depicts a side view of core 200. Core 200 includes one or more pieces of the laminate, e.g., 100 or 100a, defining a plurality of layers 204 of the absorbent laminate. For example, in the embodiment shown, a single piece of laminate 100 is folded to define an upper layer 204a, a middle layer 204b, and a lower layer 204c of the absorbent laminate. In other embodiments, multiple pieces of the absorbent laminate are stacked to define the multiple layers of the absorbent laminate, for example, with each piece defining a different layer. While the depicted embodiment includes three primary layers of the laminate, other embodiments can include any number of layers of the laminate.

In the embodiment shown in FIGS. 5 and 6, core 200 also includes an additional piece 208 of the absorbent laminate, specifically laminate 100 as shown, coupled to an upper outermost one of the sublayers of the absorbent laminate, specifically upper layer 204a. As indicated in FIG. 5, core 200—i.e., layers 204a, 204b, 204c of the absorbent laminate—have a combined width "W" and a combined length "L" that is greater than the combined width and that extends from a first end 212 of core 200 to a second end 216 of core 200. In this embodiment, additional piece 208 has a length 220 that is shorter than the combined length "L", and the additional piece is closer to first end 212 than to second end 216.

Figure 7A:
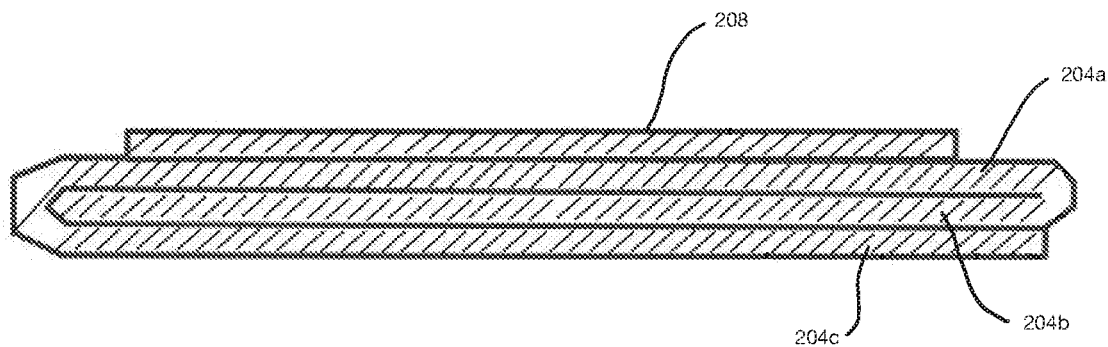
FIG. 7A depicts a schematic cross-sectional view of a first configuration of the core of FIG. 5 taken along the line 7-7 of FIG. 5.
Figure 7B:
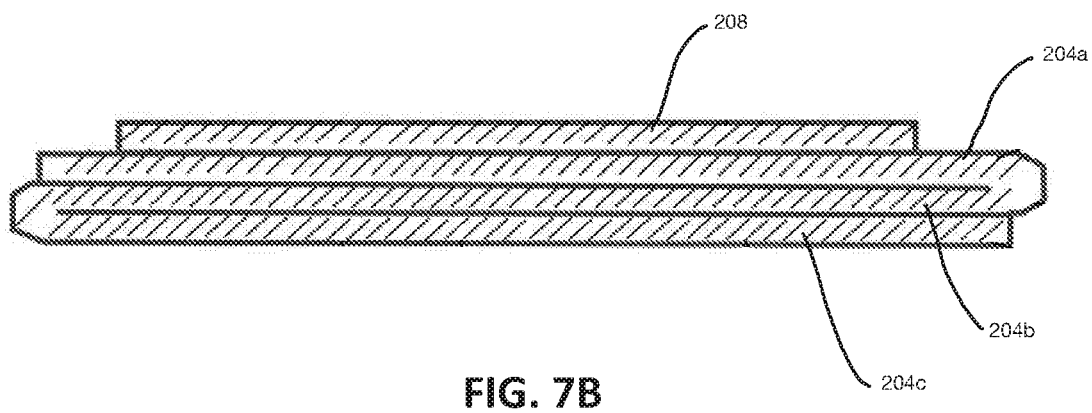
FIG. 7B depicts a schematic cross-sectional view of a second configuration of the core of FIG. 5 taken along the line 7-7 of FIG. 5.

Core 200 can be made by stacking the plurality of layers 204a, 204b, 204c. In embodiments in which a single piece of the absorbent laminate or material defines the plurality of layers, the layers can be stacked by folding the piece of absorbent laminate over itself. For example, FIG. 7A depicts a first configuration in which the piece of absorbent laminate is folded in a C-fold configuration, and FIG. 7B depicts a second configuration in which the piece of absorbent laminate is folded in a Z-fold configuration. The multiple overlying layers of absorbent laminate defines lateral channels between layers that allow fluid to flow laterally between layers, for example, to distribute fluid over a relatively larger area of each layer for absorption. Additionally, the relative position of SAP particles 216 of adjacent layers at the interface between such layers can affect surface topography each sheet and may result in valleys and corresponding micro-channels in a relatively random distribution extending laterally to further encourage dispersion of fluid between adjacent layers of absorbent laminate. The use of highly crosslinked SAP with higher gel stiffness or SAP particles with larger particle sizes can increase the surface topography of adjacent hydrated layers and thus encourage this type of channeling.

The depicted core 200 can be used in various absorbent articles, for example underwear 10 in place of core 74, that comprise a liquid-permeable topsheet; a liquid-impermeable backsheet; and a core 200 disposed between the topsheet and the backsheet. In some such articles, the article does not include a discrete ADL in addition to the core (200). In one example of such an absorbent article, the absorbent article is a bed pad, and core 200 has a width "W" of at least 12 inches and a length "L" of at least 18 inches. In some embodiments of absorbent articles including core 200, an outer sheet with anti-microbial properties and/or a smooth or lubricated surface to reduce friction is used on the surface of the product that is in contact with the skin, for example the topsheet.

FIGS. 8A, 8B, and 8C depict alternative embodiments 200a, 200b, 200c of the present folded cores. In each these embodiments, the core includes first piece 224 of the present laminates, for example laminate 100 or laminate 100a, that is folded to define a plurality of layers, and a second piece 228 of the present laminates, for example, laminate 100 or laminate 100a, that is not folded. In core 200a, first piece 224 of the laminate is folded in a C-fold configuration in which lateral portions of the piece are folded over one another such that each of the three layers have substantially equal widths. In core 200b, first piece 224 of the laminate is folded such that lateral portions of the laminate are first folded inward in two steps to define a central channel between two separate lateral regions in which the piece defines three layers of the laminate. In this embodiment of FIG. 8B, each of the lateral regions is folded in a c-fold configuration, but in other configurations, each of the lateral regions may be folded in a Z-fold configuration. Core 200c is similar to core 200b in that that laminate is folded to define two separate lateral portions, but differs from core 200b in that each of the lateral portions is folded only once to define two layers of the laminate. In these embodiments, length 232 of first piece 224 is less than, for example, from 50% to 70% of, length 236 of second piece 228. In other embodiments, second piece 228 may be folded to define multiple layers of the laminate, or may omitted such that first piece 224 defines the entire area of the core.

Referring now to FIGS. 9A and 9B; FIG. 9A depicts compression properties of a traditional fluff/SAP core over several compression cycles after absorbing fluid; and FIG. 9B depicts compression properties of core 200 over several compression cycles after absorbing fluid. As shown in FIG. 9A, the traditional fluff/SAP core recovers only about two-thirds of its initial thickness upon release of the compressive force. In contrast, and as shown in FIG. 9B, core 200 recovers over 90 percent of its initial thickness upon release of the compressive force. A pad comprised of fluff/SAP became much stiffer after the first compression cycle. This is shown by the increase in the slope of the compression-force curve in FIG. 9A. In contrast, the "TIP" core in FIG. 9B remained soft over three compression cycles. The slope of a compression-force curve at a particular stress or strain, expressed as a compression modulus, is a measure of the softness of a partially hydrated core. The lack of resiliency and softness of a partially-hydrated fluff/SAP pad may be caused by a redistribution of fluff/SAP in the X-Y plane of the pad, leaving a permanent depression at the point of compression and raised ridges of material surrounding it. After repositioning of the body mass, these ridges of hard material may generate stress concentrations against skin and promote the formation of a pressure ulcer, especially in the region of a bony protuberance. In contrast, the present materials can be exhibit improved resiliency due, for example, to combinations of the SAP gel strength properties (indicated by CRC), SAP basis weight per layer, and SAP particle size distribution. In the present multi-(sub)layered laminates, the internal substrates or non-SAP sublayers can reinforce the position of SAP particles and thereby stabilize the swollen gel during compression to maintain a soft, resilient pad over repeated cycles of compression. For example, the surface texture of internal spunlace and/or TAD tissue layers can resist spreading or lateral movement of SAP particles, thereby encouraging the SAP particles to resiliently compress.

The partially-hydrated "TIP" core including T9900 SAP for which results are shown in FIG. 9B exhibited a "strain-based" softness for a second compression cycle at a strain of 10% at $0.9 \times 10^3$ Pa when a 100 mm×100 mm section of the core was dosed with 100 ml of water. The fluff/SAP core shown in FIG. 9A, which comprised about 20% SAP, had a "strain-based" softness of $8 \times 10^3$ Pa. A "TIP" core of the same composition as that in FIG. 9B, but made with HP700E SAP, was not as soft. It had a "strain-based" softness on the second compression cycle of $34 \times 10^3$ Pa, not as good as the "TIP" core made with the T9900 SAP. However, the resiliency of the "TIP" core with P700E SAP after the first compression was 91%, nearly as good as the TIP core made with the T9900 SAP.

Figure 10:
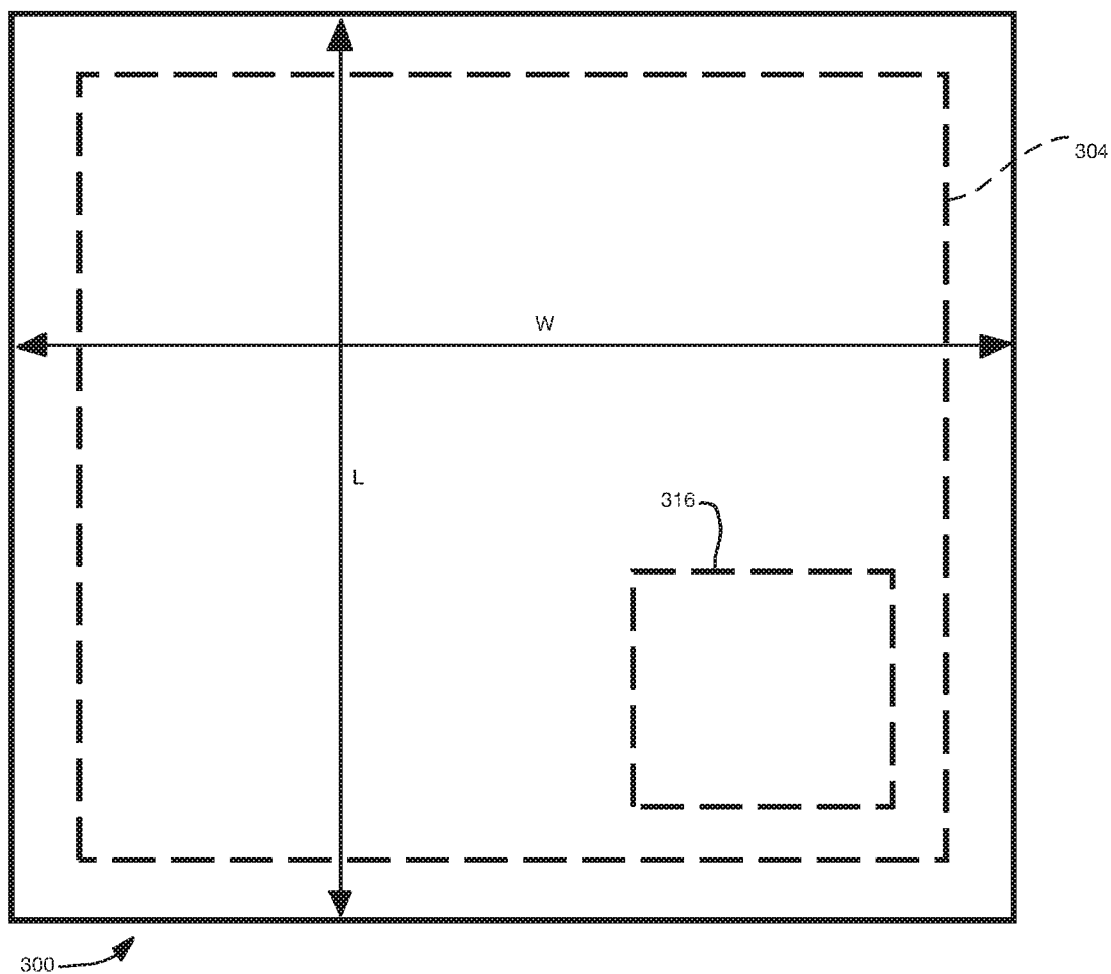
FIG. 10 depicts a plan view of an embodiment of a disposable patient-support pad.
Figure 11:
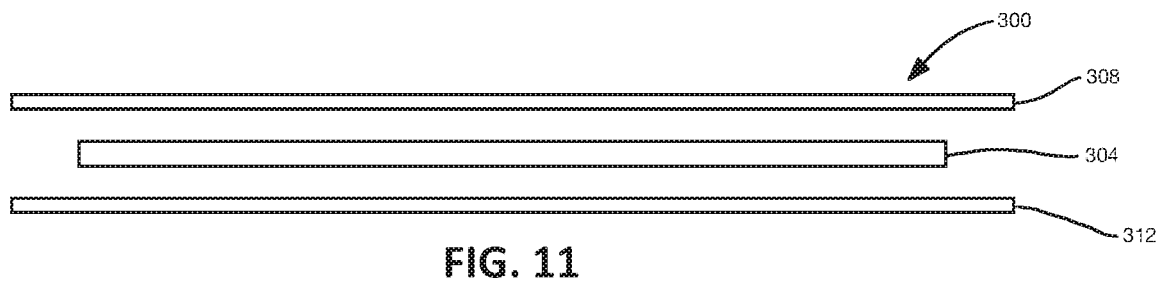
FIG. 11 depicts an exploded, cross-sectional view of a first configuration of the patient-support pad of FIG. 10.

Referring now to FIGS. 10 and 11; FIG. 10 depicts a plan view of an embodiment 300 of a disposable patient-support pad; and FIG. 11 depicts an exploded, cross-sectional view of patient-support pad 300. In this embodiment, pad 300 comprises a support core 304 and a layer 308 coupled to the support core 304. Support core 304 is similar in some respects to core 200 in that support core 304 comprises one or more pieces of the present absorbent laminates—e.g., laminate 100 or 100a—that define a plurality of layers of the absorbent laminate, similar for example to layers 204a, 204b, 204c. In the embodiment shown, a single piece of the absorbent laminate can be folded to define the plurality of layers of the absorbent laminate; however, in other embodiments, multiple pieces of the absorbent laminate are stacked to define the multiple layers of the absorbent laminate, for example, with each piece defining a different layer. Additionally, like core 200, some embodiments of support core 304 further comprise an additional piece of the absorbent laminate—e.g., laminate 100 or 100a—coupled to an upper outermost one of the sublayers of the absorbent laminate. In the embodiment shown, in which the disposable support article is a patient-support pad such as a bed pad or seat cushion, support core 304 has a width "W" of at least 8 inches and a length "L" of at least 8 inches.

In the embodiment shown in FIGS. 10 and 11, pad 300 also includes a second layer 312 bonded to first layer 308 to define a container in which support core 304 is disposed. In this embodiment, first layer 308 can be considered a topsheet because it defines a body facing surface of the pad, and second layer 312 can be considered a backsheet because it defines an outer surface of the pad that faces away from a patient or user when the pad is used. In some configurations, first layer or topsheet 308 is treated or finished to exhibit certain properties, for example, reduced friction, increased hydrophilicity, and/or increased antimicrobial properties relative to the untreated or unfinished material of the layer. In the embodiment shown, support core 304 can be wetted with liquid to swell the SAP particles prior to placing support pad 300 under a patient. Specifically, pad 300 is configured to permit liquid to be delivered to the SAP particles prior to positioning the pad under a patient. For example, as shown in FIG. 10, the depicted embodiment of pad 300 includes a container 316, for example a rupturable bladder, disposed in the enclosure and holding a volume of liquid sufficient to, when absorbed by the SAP particles of support core 304, swell at least a portion of the SAP particles to at least a desired resiliency; and the container is configured to be ruptured to release the liquid within in the enclosure to swell the SAP particles. Such rupturable bladders can be similar, for example, to those known and used in chemical cold packs sold for first aid purposes in which a liquid is released to begin an endothermic chemical reaction and reduce the temperature of the cold pack. In other embodiments, pad 300 includes an inlet, for example a sealable inlet, through which liquid can be introduced into the enclosure. Support core can be secured to first layer 308 and/or second layer 312 by a foamed adhesive, which can add a further measure of resilience to pad 300 and can further separate the support core from the respective layer to reduce the likelihood that liquid can travel to and through the respective layer and be perceived as wetness by a user.

In the embodiment shown in FIGS. 10 and 11, both of first and second layers 304, 308 are liquid-impermeable such that pad 300 will retain liquid even under pressure due to the weight of the patient, for example to prevent the liquid from seeping through the first layer at the transdermal interface with the patient's skin. In some embodiments, topsheet 308 comprises a three-dimensional polymer film, for example a film that is also resilient, that can flex to accommodate shear forces due to compression of support core 304 in use. In other embodiments, first layer or topsheet 308 comprises a breathable material such as may be used for breathable backsheets for disposable absorbent articles. For example, first layer or topsheet 308 can include, for example, an inner liquid-impermeable film and an outer nonwoven sheet that can be a nonwoven fabric. A "film" is a membrane-like layer of material formed of one or more polymers, which does not have a form consisting predominately of a web-like structure of fibers and/or other fibers. In some embodiments in which first layer or topsheet 308 is breathable, for example, an inner liquid-impermeable film of layer 308 can comprise a breathable film. The terms "breathable," "breathable film," "breathable laminate" or "breathable outer cover material"

or "breathable backsheet" refers to a film, laminate, or outer cover material having a water vapor transmission rate ("WVTR") of at least about 300 grams/m2/24 hours. Breathable materials typically rely on molecular diffusion of vapor, and are substantially liquid impermeable. Breathability of layer 308 can permit some vapor diffusion through layer to reduce moisture build up at the transdermal interface between the patient and pad 300. In other embodiments, first layer or topsheet 308 comprises a liquid-permeable material, such as an apertured film or a hydrophilic nonwoven with sufficient porosity to acquire liquid; for example, the SAP particles in support core 304 may be wetted sufficiently to swell and impart some resilience but not so much that the SAP particles are fully saturated, and can therefore absorb additional body fluids from a patient supported by the support pad.

Some embodiments of the present patient-support pads further include a second support core 304. For example, the second support core can be disposed on top of or below the first support core in a stacked configuration, or may be laterally spaced such that the first support core is configured to be disposed under a first part of a patient, for example a first heel, and the second support core is configured to be disposed under a second part of the patient, for example a second heel. In such embodiments, the patient-support pad may define separate enclosures for the support cores or may define a single enclosure in which both support cores are disposed, for example adhered or otherwise bonded to first layer or topsheet 308.

In its simplest form, other embodiments of pad 300 can omit second layer or backsheet 312; in such a configuration, the pad can be placed with support core 308 facing a water-impermeable surface such as a solid chair surface and first layer or topsheet 308 providing a patient-facing barrier, without necessarily preventing moisture from the support core from contacting or seeping out to some degree onto the supporting surface. Such embodiments may be helpful, for example, for temporary or short-term uses in which such a cushion may be desirable, but the time of use is short enough and/or other circumstances are such that the added expense of a complete enclosure is not necessarily justified.

Figure 12:
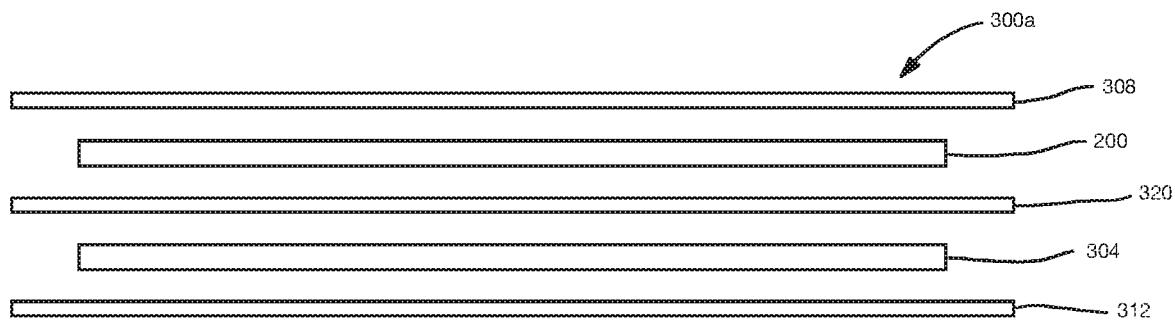
FIG. 12 depicts an exploded, cross-sectional view of a second configuration of the patient-support pad of FIG. 10.

FIG. 12 depicts an exploded, cross-sectional view of a second configuration 300a of the patient-support pad of FIG. 10. Pad 300a is similar in several respects to pad 300, with the primary exception that pad 300a includes an absorbent core 200 in addition to support core 304, and defines two compartments for the respective cores. More particularly, pad 300a includes an intermediate layer 320 dividing the enclosure into two compartments. In this embodiment, first layer 308 comprises a liquid-permeable topsheet and intermediate layer 320 comprises a liquid-impermeable material to define a first compartment in which absorbent core 200 is disposed to receive body fluid exudates from a patient disposed on pad 300a. Intermediate sheet 320 and backsheet 312 are both liquid-impermeable to contain liquid in the compartment in which support core 304 is disposed. As with pad 300, pad 300a is configured to permit liquid to be delivered to support core 304 prior to positioning pad 300a under a patient, for example, via a container 316 or separate inlet as described above. In some embodiments, intermediate layer 320 comprises a three-dimensional polymer film, for example a film that is also resilient, that can flex to accommodate shear forces due to compression of support core 304 in use. In this embodiment, absorbent core 200 can perform the traditional absorbent functions of a conventional bed pad, while support core 300 can independently perform the support functions of a conventional patient-support cushion or seat cushion.

Figure 13:
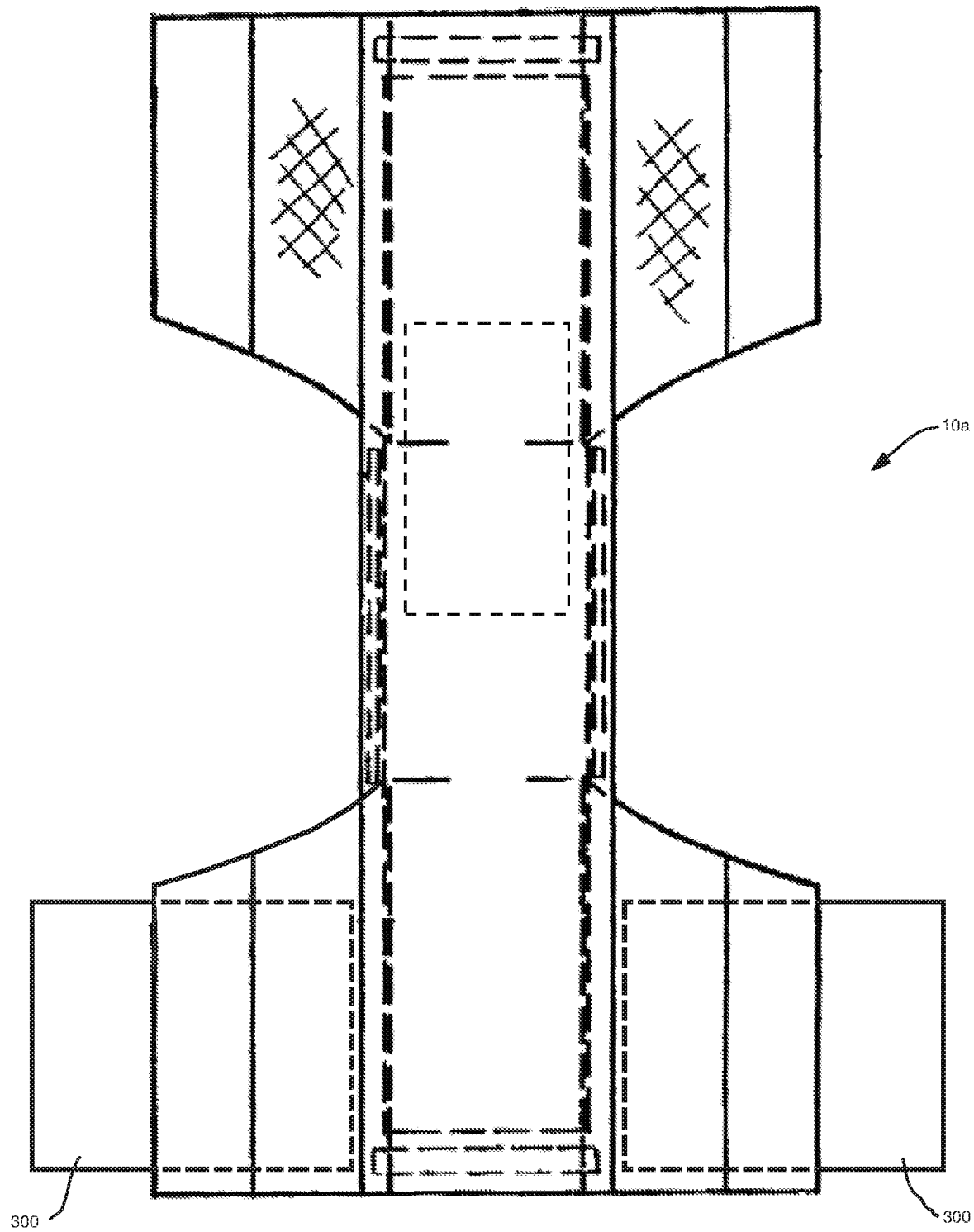
FIG. 13 depicts a bottom plan view of a disposable absorbent article, specifically adult protective underwear, including patient-support pads and in an open configuration.

FIG. 13 depicts a bottom plan view of a disposable absorbent article 10a, specifically adult protective underwear, including patient-support pads 300 and in an open configuration. Underwear 10a is substantially similar to underwear 10 with the exception of patient-support pads 300, which are similar to those described above but sized for the depicted configuration. In this embodiment, patient-support pads 300 are shaped to extend around a wearer's hips to provide cushioning to distribute forces and reduce local maxima of TIP and thereby reduce the likelihood of bed sores. In other embodiments, additionally or alternatively, patient-support pads 300 can be sized and/or shaped to overlie the patient's buttocks.

In use, liquid can be delivered to the support core 304 of the patient-support pads 300 or 300a prior to placing the patient-support pads 304 under a portion of a patient, and the support core(s) allowed to absorb a sufficient volume of the liquid to increase the resilience in compression of the support core. The liquid used to swell the SAP particles can comprise water, saline, or the like; and, such liquid in some instances comprises an antimicrobial additive and/or skin care additive such as vitamin E or the like.

Figure 14:
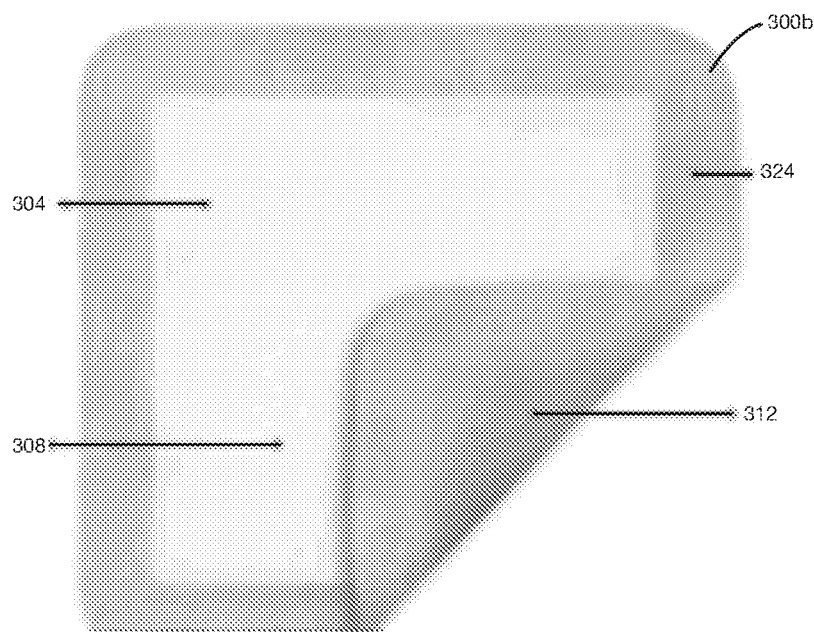
FIGS. 14-16 depict various views of embodiments of the present patient-support pads.
Figure 15:
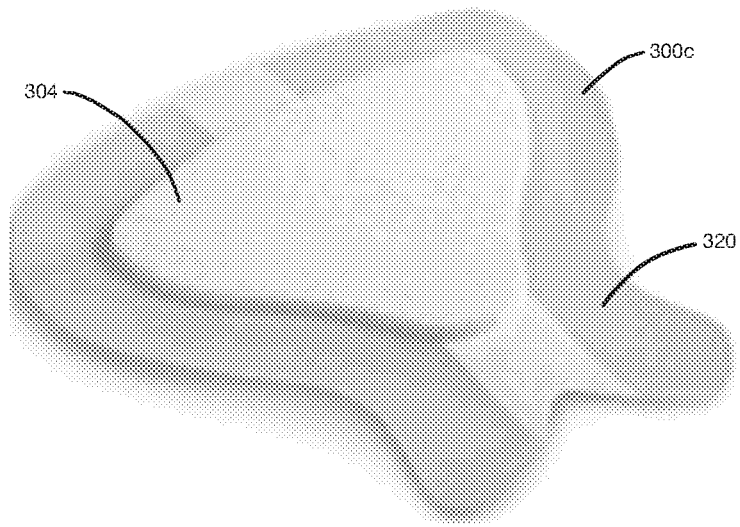
Figure 16:
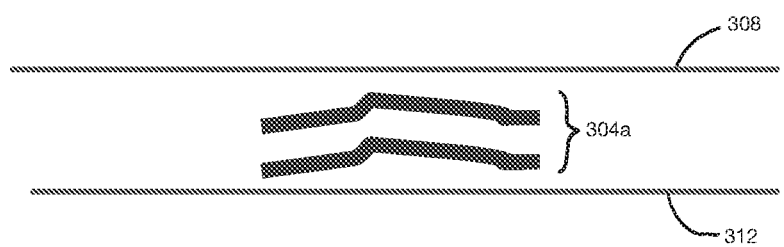

FIGS. 14-16 depict various views of embodiments of the present patient-support pads. More particularly, FIG. 14 depicts a top view of a patient support pad 300b that is sized and/or contoured to overlie a portion of a patient's body, for example, a hip, a shoulder, an elbow, or the head. Pad 300b is similar in constructions to pad 300 of FIG. 11, with the exception that pad 300a includes an adhesive 324 that is configured to couple the pad to a user. For example, adhesive 320 can comprise a dermal adhesive configured to adhere the pad to directly to a patient's skin, or adhesive 324 can be configured to adhere the pad to an interior surface of a patient's garment or absorbent article. FIG. 15 depicts a pad 300c that is similar in construction to pad 300b, with the exception that pad 300c is contoured to overlie a patient's sacrum or heel. FIG. 16 depicts a cross-sectional view of one optional configuration for any of pads 300, 300a, 300b, and 300c. In the configuration of FIG. 16, a support core 304a includes multiple layers of one of the present absorbent laminates, for example with the layers not bonded to one another and thereby permitted to slide relative to one another. In the depicted embodiment, the support core spans only a particular zone of the pad, for example spans less than 50% of an overall lateral dimension of the pad.

EXAMPLES

Several prototypes of the laminate depicted in FIG. 3 were produced and tested, with the materials and basis weights listed below in Table 1 below.

TABLE 1

Prototype Laminate Construction

| COMPONENT | PROTO-TYPE 1 basis weight | PROTO-TYPE 2 basis weight | PROTO-TYPE 3 basis weight |
| --- | --- | --- | --- |
| Tissue Facing (124) | 17 gsm | 17 gsm | 17 gsm |
| Adhesive (120) | 2 gsm | 2 gsm | 4 gsm |
| SAP (116) | 50 gsm | 56 gsm | 80 gsm |
| Nonwoven (112) | 20 gsm | 20 gsm | 20 gsm |
| Adhesive (120) | 2 gsm | 2 gsm | 1 gsm |

TABLE 1-continued

Prototype Laminate Construction

| COMPONENT | PROTOTYPE 1 basis weight | PROTOTYPE 2 basis weight | PROTOTYPE 3 basis weight |
|---|---|---|---|
| SAP (116) | 50 gsm | 56 gsm | 21 gsm |
| Tissue Facing (128) | 17 gsm | 17 gsm | 17 gsm |
| ALL | 158 gsm | 170 gsm | 160 gsm |

The tissue used for the fourth sublayer 124 and fifth sublayer 128 was 17 gram per square meter (gsm) 3995 tissue from Dunn Paper. The adhesive (120) in first sublayer 104 and second sublayer 108 was E60W from Savare Specialty Adhesives. The SAP (116) in first sublayer 104 and second sublayer 108 was T9900 from BASF. The nonwoven used for sublayer 112 was a 20 gsm, 100% Viscose spunlace nonwoven from Jacob-Holm Group. Although the SAP and adhesive are separately listed, the SAP and adhesive were applied as a mixture for each sublayer 104, 108.

Each of these three prototypes were also subjected to certain tests to determine mechanical properties of their respective constructions. The results of these tests are listed in Table 2 below.

TABLE 2

Prototype Laminate Test Data

| | Value: | | | |
|---|---|---|---|---|
| | Tensile Strength (N/50 mm) | | Caliper (mm) | |
| Statistic (n + 3) | Average | s | Average | s |
| PROTOTYPE 1 | 44.2 | 1.9 | 1.19 | 0.007 |
| PROTOTYPE 2 | 40.3 | 1.4 | 1.23 | 0.015 |
| PROTOTYPE 3 | 43.3 | 1.9 | 1.18 | 0.007 |

The tensile strength was measured dry in the machine direction (MD), using a Zwick Model Z005 Materials testing frame with TestXpert software. Specifically, 50 mm×240 mm samples of each prototype laminate were cut and clamped into the jaws of the tensile tester with the 240 mm dimension oriented parallel to the pulling direction of the tensile tester. The jaws were then moved apart at a rate of 100 mm per minute until the sample broke or until a jaw separation of 500 mm is achieved, and the force in Newtons recorded at the point at which the sample broke or the force required to further separate the jaws dropped below 95% of the maximum force. Caliper was measured with an Emveco Electronic Microgauge Model 200 A at a pressure of 0.0725 pounds per square inch (psi).

Core Prototype & Tests

Core prototypes utilizing the above-described laminate prototypes were constructed and tested for acquisition and runoff performance. For control/comparison, traditional fluff/SAP diaper cores were subject to similar acquisition and runoff performance.

For acquisition testing, the Fluid Intake Flowback and Evaluation apparatus shown in and described with reference to FIGS. 5 and 6 of U.S. Pat. No. 5,147,343 to Kellenberger, lines 21-65 of column 10 of which patent are incorporated by reference herein. The sample core or diaper was placed on the 3-inch×6-inch elevated platform according to the position described in this Kellenberger patent to center the dosing tube over the product target. An 880 g lid with 5.1 cm internal diameter (ID) dosing tube was placed on the core on alignment pins centering the dosing tube over the elevated platform.

A 100 milliliter (mL) dose of 0.9% saline (with 12 drops of McCormick Green food coloring per 20 liters of saline) was added to the dosing tube with a graduated cylinder and the time required for the liquid to drain into the core was recorded as the acquisition time. After 30-minutes, the top of the apparatus was removed and a stack of 10 Whatman No. 4, 70 mm diameter filter paper circles were placed on the center of the target of the core, and a 0.7 psi weight was placed on top of the filter paper circles for exactly 2 minutes. The filter paper circles were then removed and weighed, and the liquid absorbed by the filter papers was recorded as rewet. The doser plate was then replaced, and the above steps were repeated with a second 100 mL dose of saline. This testing was performed three times for each core prototype and diaper core, and the average and standard deviations were calculated for each core prototype or diaper core.

A core prototype was prepared by stacking two 200 mm×300 mm pieces of Prototype 1 laminate (described above), and folding them longitudinally to make a 100 mm×300 mm core with 4 plies of material. A piece of 15 gsm surfactant treated spunbond polypropylene diaper topsheet was placed on the top of this folded core prototype to prevent liquid from disturbing the surface of the core. A first control/comparison variant was prepared by cutting away the elastics around the perimeter of the core of size large, conventional fluff/SAP-core diapers to permit the diapers to lay flat in the apparatus. A second control/comparison variant was prepared by carefully removing the nonwoven acquisition-distribution layer (ADL) using a heat gun to separate the ADL from the topsheet of similar size large, conventional fluff/SAP-core diapers, after which the topsheet was carefully replaced over the core. All three variants were tested according to the procedure described above. The acquisition time data is recorded below Table 3 below. Particularly after the prototype core was wetted (after the first acquisition), the prototype core—without a separate ADL—exhibited acquisition times consistent with conventional diaper cores with discreet ADLs. The prototype cores also had a noticeably smaller caliper relative to the conventional cores. Specifically, the conventional fluff/SAP diaper cores had a caliper of about 5.4 mm in the target zone, whereas the prototype cores had a caliper of about 3.7 mm in the target zone.

TABLE 3

Acquisition Test Data

| | statistic (n = 3) | 1st 100 mL Acquisition | 2nd 100 mL Acquisition |
|---|---|---|---|
| Core Prototype (4 plies) | average= | 30.7 sec. | 16.4 sec. |
| | s= | 1.5 | 0.3 |
| Control 1 (Large Diaper, with ADL) | average= | 21.7 sec. | 19.4 sec. |
| | s= | 0.8 | 2.4 |
| Control 2 (Large Diaper, no ADL) | average= | 39.4 sec. | 38.4 sec. |
| | s= | 9.1 | 9.0 |

For acquisition testing—intended to illustrate the effects of the capillary characteristics of the core to spread liquid through the core and prevent it from leaking out before SAP has time to absorb—a 45-degree runoff apparatus was constructed. The apparatus included a sample support surface angled at 45 degrees relative to a horizontal support surface. The sample support surface is sized to support a 150 mm×100 mm core sample at a slope of 45 degrees while a dosing tube with a ⅛-inch ID is centered above the sample, with the discharge of the dosing tube disposed 25-mm above the sloping sample support surface. The 150 mm dimension of the sample is oriented along the slope, and the sample is held in place on the sample support plate by six sharp pins protruding outward from the sample support surface. The sample rests on the bottom row of pins to locate it relative to the dosing tube, and the rest of the pins puncture the sample core and thereby hold it in place along the sample support surface. In operation, dosing tube dispenses 50 ml 0.9% saline in about 6-seconds using a gravity feed from a funnel. Any of the dosed liquid that is not absorbed by the sample runs down the sample support surface to an collection trough at the bottom of the sample support surface. The collection trough is also angled to direct the liquid into a small beaker to be collected as runoff. The runoff was then poured from the beaker into a 100 ml graduated cylinder and the volume of the runoff is recorded.

Prototype cores were constructed by stacking 4—150 mm×100 mm plies of Prototype 1 laminate (described above). These four plies were then wrapped in a 15 gsm spunbond nonwoven diaper topsheet and the topsheet material stapled around the perimeter to prevent material of the laminate from leaking out when wetted.

For control/comparison, size large, conventional fluff/SAP-core diapers were cut transversely at a point 150 mm below the front waist of the core. Scissors were used to cut away the elastic materials from around the perimeter of the core but the side bonds retained to contain the core when wet. The core was then tucked back into the transverse cut edge and the backsheet was stapled to the topsheet to retain the core material after wetting.

Five (N=5) of each of the prototype cores and conventional diaper cores were dosed with 50 mL saline, the runoff was recorded, and then each was allowed to equilibrate 30-minutes before a subsequent dose, and the process repeated for five (5) doses. The measured runoff data is shown in Table 4 below. As shown, the prototype cores exhibited runoff comparable to that of the conventional diapers for the first dose, rather than exhibiting poorer runoff results as would typically be expected of thinner—e.g., pulp-less—cores.

Given the smaller void volume of the Example 1 core, due to its thinness, it is difficult to obtain runoff values similar to that of a conventional fluff SAP diaper which is thicker.

TABLE 4

Runoff Test Data

| | Statistic (n = 5) | 1st dose | 2nd dose | 3rd dose | 4th dose | 5th dose |
|---|---|---|---|---|---|---|
| Prototype Core (4 plies 100 mm × 150 mm) | Average = s = | 20.2 g 1.6 | 7.4 g 1.1 | 10.8 g 1.1 | 15 g 1.0 | 19.6 g 1.1 |
| Size Large Diaper (150 mm × core width) | Average = s = | 18 g 4.2 | 20.4 g 7.6 | 20.6 g 4.8 | 28.4 g 3.4 | 30.2 g 2.3 |

Additional Core Prototypes and Resiliency/Softness Testing

Several prototypes of the laminate depicted in FIG. 3 were produced and tested, with the materials and basis weights listed below in Table 5 below. To investigate the effects of SAP type and middle substrate (112) materials on resiliency (recovery of thickness after compression) and softness (compression modulus, K), two different SAPs and two different middle substrates were used to make four additional prototype laminates, as listed in Table 5.

TABLE 5

Additional Prototype Laminate Construction

| COMPONENT | PROTOTYPE 4 basis weight | PROTOTYPE 5 basis weight | PROTOTYPE 6 basis weight | PROTOTYPE 7 basis weight |
|---|---|---|---|---|
| Tissue Facing (124) | 17 gsm | 17 gsm | 17 gsm | 17 gsm |
| Adhesive (120) | 2.5 gsm | 2.5 gsm | 2 gsm | 2.5 gsm |
| SAP (116) | 50 gsm BASF T9900 | 50 gsm BASF T9900 | 50 gsm Sumitomo HP700E | 50 gsm Sumitomo HP700E |

TABLE 5-continued

Additional Prototype Laminate Construction

| COMPONENT | PROTOTYPE 4 basis weight | PROTOTYPE 5 basis weight | PROTOTYPE 6 basis weight | PROTOTYPE 7 basis weight |
|---|---|---|---|---|
| Middle substrate (112) | 28 gsm viscose spunlace | 21 gsm through-air dried tissue | 28 gsm viscose spunlace | 21 gsm through-air dried tissue |
| Adhesive (120) | 2.5 gsm | 2.5 gsm | 2 gsm | 2.5 gsm |
| SAP (116) | 50 gsm BASF T9900 | 50 gsm BASF T9900 | 50 gsm Sumitomo HP700E | 50 gsm Sumitomo HP700E |
| Tissue Facing (128) | 17 gsm | 17 gsm | 17 gsm | 17 gsm |

The tissue used for the fourth sublayer 124 and fifth sublayer 128 was 17 gram per square meter (gsm) 3995 tissue from Dunn Paper. The adhesive (120) in first sublayer 104 and second sublayer 108 was E60W from Savare Specialty Adhesives. Although the SAP and adhesive are separately listed, the SAP and adhesive were applied as a mixture for each sublayer 104, 108.

From these four additional prototype laminates, four additional core prototypes were formed in the manner described above with three layers of the respective prototype laminate wrapped in a nonwoven topsheet material.

Resiliency and softness of the absorbent cores were measured using an Model 5943 Instron compression/tension apparatus equipped with a 1 kN compression/tension load cell. Test samples were constructed using a 100 mm×100 mm section of an absorbent core (fluff/SAP or multiple layers of laminate) that was attached to a typical poly backsheet material with a light application of hot melt adhesive. A 12 gsm polypropylene topsheet was placed on the surface of the absorbent core. Test samples were hydrated uniformly with either 100 mL or 145 mL of tap water and equilibrated for 30 min. at 22° C./50% relative humidity before compression. After equilibration the sample was placed between two Instron compression plates (150 mm diameter) that were initially separated by a distance greater than the swollen thickness of the sample. The lower plate was rigidly attached to the base of the Instron apparatus and the upper plate was attached to a compression load cell. The samples were subjected to three successive compression/decompression cycles at a crosshead speed of 10 mm per minute. Maximum compression was set to a compressive force of either 20N or 50N. Thickness of a sample was defined as the spacing of the compression plates when compressing a sample at a force of 2 N.

The resiliency and softness relevant for an absorbent core of an absorbent product was determined by dosing a sample with 100 mL of tap water and cycling to a maximum compression force of 20N. Resiliency was defined as the % recovery in sample thickness after the first compression cycle. Higher recovery values are considered to be generally better. For example, if a sample returned to its original swollen thickness after one cycle of compression, the % recovery would be 100%. A "strain-based" measure of softness was defined as the compression modulus (that is, the slope of the compression force vs. strain curve expressed in Pa) at 10% compressive strain on the second compression cycle. Strain is the reduction in thickness on compression divided by the sample thickness at the beginning of a compression cycle. Smaller values of compression modulus indicate a softer core.

The resiliency and softness relevant for an absorbent core of a disposable patient-support article was determined by dosing a sample with 145 mL of tap water and cycling to a maximum compression force of either 20N or 50N. Resiliency was defined as the % recovery in sample thickness after the first compression cycle. A "stress-based" measure of softness was defined as the compression modulus at a maximum force of either 20 N or 50 N (i.e. at a maximum pressure of either $2 \times 10^3$ Pa or $5 \times 10^3$ Pa for a 100 mm×100 mm sample).

Resiliency and softness was measured for four prototypes made with T9900 SAP or HP700E SAP, and middle substrates of 28 gsm viscose spunlace or 21 gsm through-air-dried tissue. Specifically, for resiliency and softness, each core was partially hydrated with 145 mL of water and then subjected to multiple applications of compressive force cycling between 2 N and 50 N over an area of 100 mm×100 mm. After each compression cycle, the percentage of original thickness was measured upon removal of the compressive force. The results of these tests are listed in Table 6 below.

The hydrated thickness of prototype cores made with laminates containing T9900 SAP was between 28% and 48% greater than the hydrated thickness of prototype cores made with the HP700E SAP. The HP700E SAP had a finer particle size distribution than that of the T9900 SAP, resulting in a higher packing density for the HP700E SAP. Another difference between the SAPs is their centrifuge retention capacities or CRC, which were 33 g/g for the T9900 SAP and 47 g/g for the HP700E SAP, as determined by WSP 241.2 method.

Resiliency (i.e. Recovery of Thickness after Cycles 1, 2 & 3) for all four possible combinations of SAP and middle substrates (112) were comparable for prototype cores with three layers of absorbent laminate. Resiliency ranged from 87% to 89% for the first compression cycles and 84% to 88% for the third compression cycles. All prototype cores provided much better values of resiliency than those obtained for a fluff/SAP core. Specifically, resiliency of partially hydrated fluff/SAP cores is typically less than 70% when compressed to a pressure of between $2 \times 10^3$ Pa (0.3 psi) and $5 \times 10^3$ Pa (0.7 psi).

Softness—i.e., Compression Modulus at $5 \times 10^3$ Pa—was lower for the prototype cores made with the T9900 SAP. Specifically, the Compression Modulus of a partially hydrated prototype core containing T9900 SAP was $72 \times 10^3$ Pa at a pressure of $5 \times 10^3$ Pa. By comparison, Softness of partially hydrated fluff/SAP cores are typically greater than $70 \times 10^3$ Pa at this pressure. Comparable values of softness were obtained for prototype cores made with laminates containing spunlace and tissue internal layers.

TABLE 6

Resiliency and Softness Data

| Prototype | Hydrated Thickness (mm) | Recovery of Thickness (%) | | | Compression Modulus, K ($\times 10^3$ Pa) | | |
|---|---|---|---|---|---|---|---|
| | | after Cycle 1 | after Cycle 2 | after Cycle 3 | after Cycle 1 | after Cycle 2 | after Cycle 3 |
| 4 | 26.3 | 88 | 88 | 86 | 47.3 | 71.7 | 75.2 |
| 5 | 26.9 | 87 | 85 | 84 | 41.8 | 72.5 | 75.9 |
| 6 | 20.6 | 88 | 87 | 86 | 61.7 | 124.9 | 132.7 |
| 7 | 18.2 | 89 | 88 | 88 | 74.7 | 146.0 | 156.8 |

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. An absorbent laminate comprising:
a first sublayer comprising super-absorbent polymer (SAP) particles and an adhesive supporting the SAP particles in a porous matrix;
a second sublayer comprising SAP particles and an adhesive supporting the SAP particles in a porous matrix; and
a third sublayer disposed between, and bonded to each of, the first and second layers, wherein the third sublayer is not itself a laminate, and wherein the third sublayer comprises a nonwoven web having a basis weight of from 6 gsm to 80 gsm,
wherein the basis weight of the SAP particles of the first sublayer is different than the basis weight of the SAP particles of the second sublayer,
wherein the SAP particles of one of the first sublayer or the second sublayer have a basis weight of from 20 grams per square meter (gsm) to 80 gsm, and
wherein the SAP particles of the other of the first sublayer or the second sublayer have a basis weight of less than 50 gsm.

2. The absorbent laminate of claim 1, where the third sublayer comprises a spunlace nonwoven web having a basis weight of from 20 gsm to 80 gsm.

3. The absorbent laminate of claim 1, where the third sublayer comprises a tissue with a basis weight of from 15 gsm to 35 gsm.

4. The absorbent laminate of claim 1, where the third sublayer comprises regenerated cellulosic fibers.

5. The absorbent laminate of claim 1, further comprising:
a fourth sublayer bonded to the first sublayer such that the first sublayer is disposed between the fourth sublayer and the third sublayer, the fourth sublayer comprising tissue; and
a fifth sublayer bonded to the second sublayer such that the second sublayer is disposed between the fifth sublayer and the third sublayer, the fifth sublayer comprising tissue.

6. The absorbent laminate of claim 5, where the absorbent laminate has a caliper of less than 1.3 millimeters (mm).

7. The absorbent laminate of claim 5, where the tissue of at least one of the fourth and fifth sublayers is creped and/or through-air dried.

8. An absorbent core for a disposable absorbent article, the absorbent core comprising:
one or more pieces of the absorbent laminate of claim 1 defining a plurality of layers of the absorbent laminate.

9. The absorbent core of claim 8, where a single piece of the absorbent laminate is folded to define the plurality of layers of the absorbent laminate.

10. The absorbent core of claim 8, where multiple pieces of the absorbent laminate are stacked to define the multiple layers of the absorbent laminate.

11. The absorbent core of claim 8, where the absorbent core is configured to exhibit a resiliency greater than 70% when partially hydrated.

12. The absorbent core of claim 8, where the absorbent core is configured to exhibit a Stress-Based Softness for a second compression cycle, at a pressure of $5 \times 10^3$ Pa, of less than $150 \times 10^3$ Pa when a 100 mm×100 mm section of the absorbent core is dosed with 145 milliliters (mL) of water.

13. The absorbent core of claim 8, where the absorbent core is configured to exhibit a Strain-Based Softness for a second compression cycle, at a strain of 10%, of less than $4 \times 10^{-3}$ Pa when a 100 mm×100 mm section of the absorbent core is dosed with 100 milliliters (mL) of water.

14. A disposable absorbent article comprising:
a liquid-permeable topsheet;
a liquid-impermeable backsheet; and
an absorbent core disposed between the topsheet and the backsheet, the absorbent core comprising one or more pieces of the absorbent laminate of claim 1 defining a plurality of layers of the absorbent laminate.

15. The absorbent article of claim 14, where the absorbent article does not include a discrete acquisition-distribution layer in addition to the absorbent core.

16. The absorbent article of claim 14, where the absorbent article is a bed pad, and the absorbent core has a width of at least 12 inches and a length of at least 18 inches.

17. A disposable patient-support article comprising:
- a support core comprising one or more pieces of the absorbent laminate of claim 1 that define a plurality of layers of the absorbent laminate; and
- a liquid impermeable layer coupled to the support core;
- where the support core has a width of at least 8 inches and a length of at least 8 inches.

18. The patient-support article of claim 17, where the liquid-impermeable layer is a backsheet, and the patient-support article further comprises:
- a topsheet;
- where the support core is disposed between the backsheet and the topsheet such that the backsheet and topsheet form an enclosure in which the support core is disposed.

19. The patient-support article of claim 17, where the backsheet and topsheet cooperate to define at least a portion of a chassis of a bed pad or underpad.

20. The absorbent core of claim 8, further comprising:
- an additional piece of the absorbent laminate coupled to an outermost one of the sublayers of the absorbent laminate, the additional piece of the absorbent laminate comprising:
- a first sublayer comprising super-absorbent polymer (SAP) particles and an adhesive supporting the SAP particles in a porous matrix, the SAP particles in the first sublayer having a basis weight of from 20 grams per square meter (gsm) to 130 gsm;
- a second sublayer comprising SAP particles and an adhesive supporting the SAP particles in a porous matrix, the SAP particles in the second sublayer having a basis weight of from 20 gsm to 130 gsm; and
- a third sublayer disposed between, and bonded to each of, the first and second layers, the third sublayer comprising a nonwoven web, the nonwoven web having a basis weight of from 6 gsm to 80 gsm;
- a fourth sublayer bonded to the first sublayer such that the first sublayer is disposed between the fourth sublayer and the third sublayer, the fourth sublayer comprising tissue; and
- a fifth sublayer bonded to the second sublayer such that the second sublayer is disposed between the fifth sublayer and the third sublayer, the fifth sublayer comprising tissue.

\* \* \* \* \*